(12) United States Patent
Cai et al.

(10) Patent No.: US 7,611,621 B2
(45) Date of Patent: Nov. 3, 2009

(54) DISPOSABLE OXYGEN SENSOR AND METHOD FOR CORRECTING OXYGEN EFFECT ON OXIDASE-BASED ANALYTICAL DEVICES

(75) Inventors: Xiaohua Cai, Needham, MA (US);
Kara Alesi, Winchester, MA (US);
Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 872 days.

(21) Appl. No.: 11/160,193

(22) Filed: Jun. 13, 2005

(65) Prior Publication Data
US 2006/0278537 A1    Dec. 14, 2006

(51) Int. Cl.
*G01N 27/327*    (2006.01)
*C12Q 1/26*    (2006.01)
*C12Q 1/28*    (2006.01)
*C12Q 1/54*    (2006.01)

(52) U.S. Cl. .............................. 205/777.5; 204/403.04; 204/403.01; 205/782; 205/792

(58) Field of Classification Search .................. 204/403.04–403.15; 205/777.5, 792, 782; 600/347; 435/4, 14, 25, 28
See application file for complete search history.

(56) References Cited

U.S. PATENT DOCUMENTS

| | | | |
|---|---|---|---|
| 4,311,151 A | 1/1982 | Hagihara | |
| 4,431,004 A * | 2/1984 | Bessman et al. | ............ 600/347 |
| 4,466,879 A | 8/1984 | Ho et al. | |
| 4,476,870 A | 10/1984 | Peterson et al. | |
| 4,672,971 A | 6/1987 | Otten | |
| 4,930,506 A | 6/1990 | Ullrich | |
| 5,007,424 A | 4/1991 | Ahsbahs et al. | |
| 5,030,333 A | 7/1991 | Clark, Jr. | |
| 5,089,421 A | 2/1992 | Dieffenbach | |
| 6,190,612 B1 | 2/2001 | Berger et al. | |
| 6,258,229 B1 | 7/2001 | Winarta et al. | |
| 6,287,451 B1 | 9/2001 | Winarta et al. | |
| 6,299,757 B1 | 10/2001 | Feldman et al. | |

(Continued)

FOREIGN PATENT DOCUMENTS

WO    WO 03012422 A1 *    2/2003

OTHER PUBLICATIONS

Polgar et al., "Measurement of oxygen tension in unstirred blood with a platinum electrode," J. Appl. Physiol., 1960, 706-11, 15.

(Continued)

*Primary Examiner*—Kaj K Olsen
*Assistant Examiner*—Kourtney R Salzman
(74) *Attorney, Agent, or Firm*—Robert R. Deleault, Esq.; Mesmer & Deleault, PLLC

(57) ABSTRACT

A system and method for correcting the oxygen effect on oxidase-based analyte sensors includes an oxygen sensor with a working electrode, a reagent matrix disposed on at least the working electrode that contains a reduced form of a redox mediator, an oxidase and a peroxidase, an oxidase-based analyte sensor, a means for determining the oxygen concentration in a portion of a fluid sample using the oxygen sensor, means for determining an analyte concentration in another portion of the fluid sample using the oxidase-based analyte sensor, and means for using the oxygen concentration in the fluid sample to determine a corrected analyte concentration in the fluid sample.

33 Claims, 16 Drawing Sheets

U.S. PATENT DOCUMENTS

| | | |
|---|---|---|
| 6,767,441 B1 | 7/2004 | Cai et al. |
| 6,773,564 B1 | 8/2004 | Yugawa et al. |
| 6,837,976 B2 | 1/2005 | Cai et al. |
| 2003/0196894 A1 | 10/2003 | Cai et al. |

OTHER PUBLICATIONS

Mayers et al., "A rapid method for measuring blood oxygen content utilizing the oxygen electrode," J. Appl. Physiol., 1966, 1393-96, 21.

Fenner, "Oxygen monitoring in neonatal medicine," Biotelemetry, 1974, 227-38, 1.

Crockard et al., "Measurements of oxygen tension in the cerebral coretex of baboons," J. Neurol. Sci., 1976, 17-28, 27.

Rithalia et al., "The performance characteristics of an intra-arterial oxygen electrode," Intensive Care Med., 1981, 305-7, 7.

Hagihara et al., "Intravascular oxygen monitoring with a polarographic oxygen cathode," J. Biomed. Eng., 1981, 9-16, 3.

Nilsson et al., "Polarographic PO2 sensors with heparinized membranes for in vitro and continuous in vivo registration," Scand. J. Clin. Lab. Invest., 1981, 557-63, 41.

Claremont et al., "Continuous monitoring of blood PO2 in extracorporeal systems. An in vitro evaluation of a re-usable oxygen electrode," Anaesthesia, 1984, 362-9, 39.

Severinghaus et al., "History of blood gas analysis. IV. Leland Clark's oxygen electrode," J. Clin. Monit., 1986, 125-39, 2.

Nagaoka et al., "Antithrombogenic PO2 sensor for continuous intravascular oxygen monitoring," Biomaterials, 1990, 414-8, 11.

Suzuki et al., "Fabrication of a sensing module using micromachined biosensors," Biosens. Bioelectron, 2001, 725-33, 16.

Golde et al., "The oxygen optode: an improved method of assessing flap blood flow and viability," J. Otolaryngol., 1994, 138-44, 23.

* cited by examiner

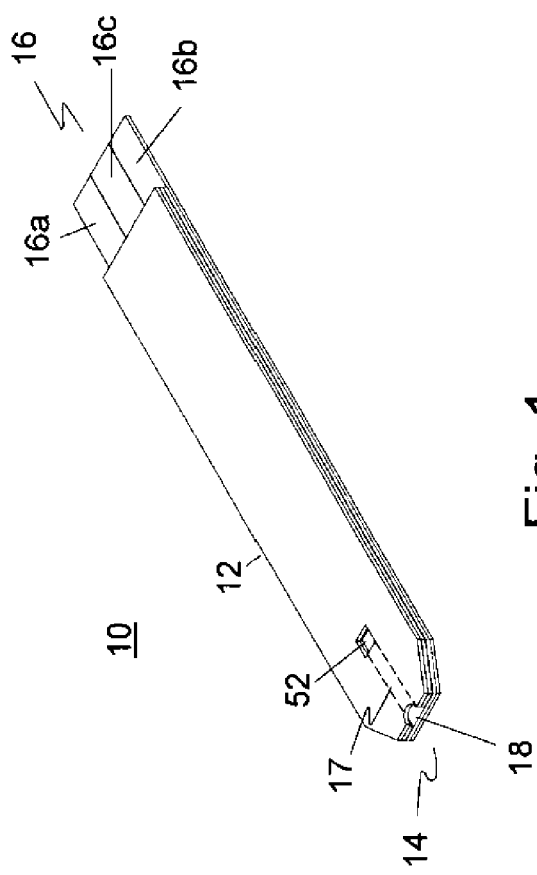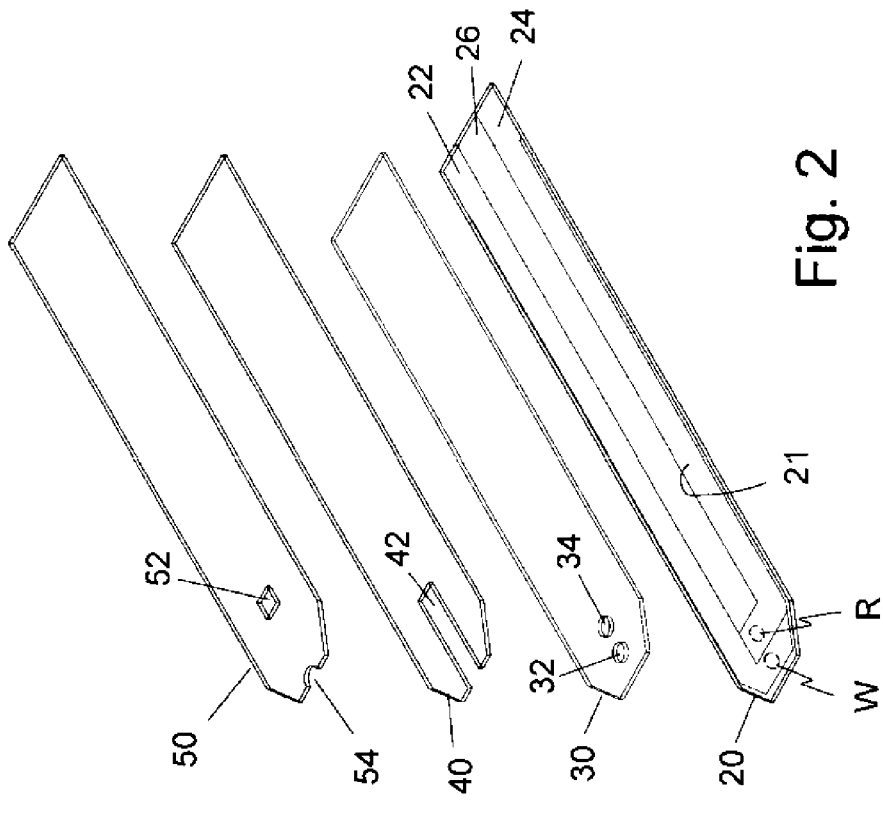

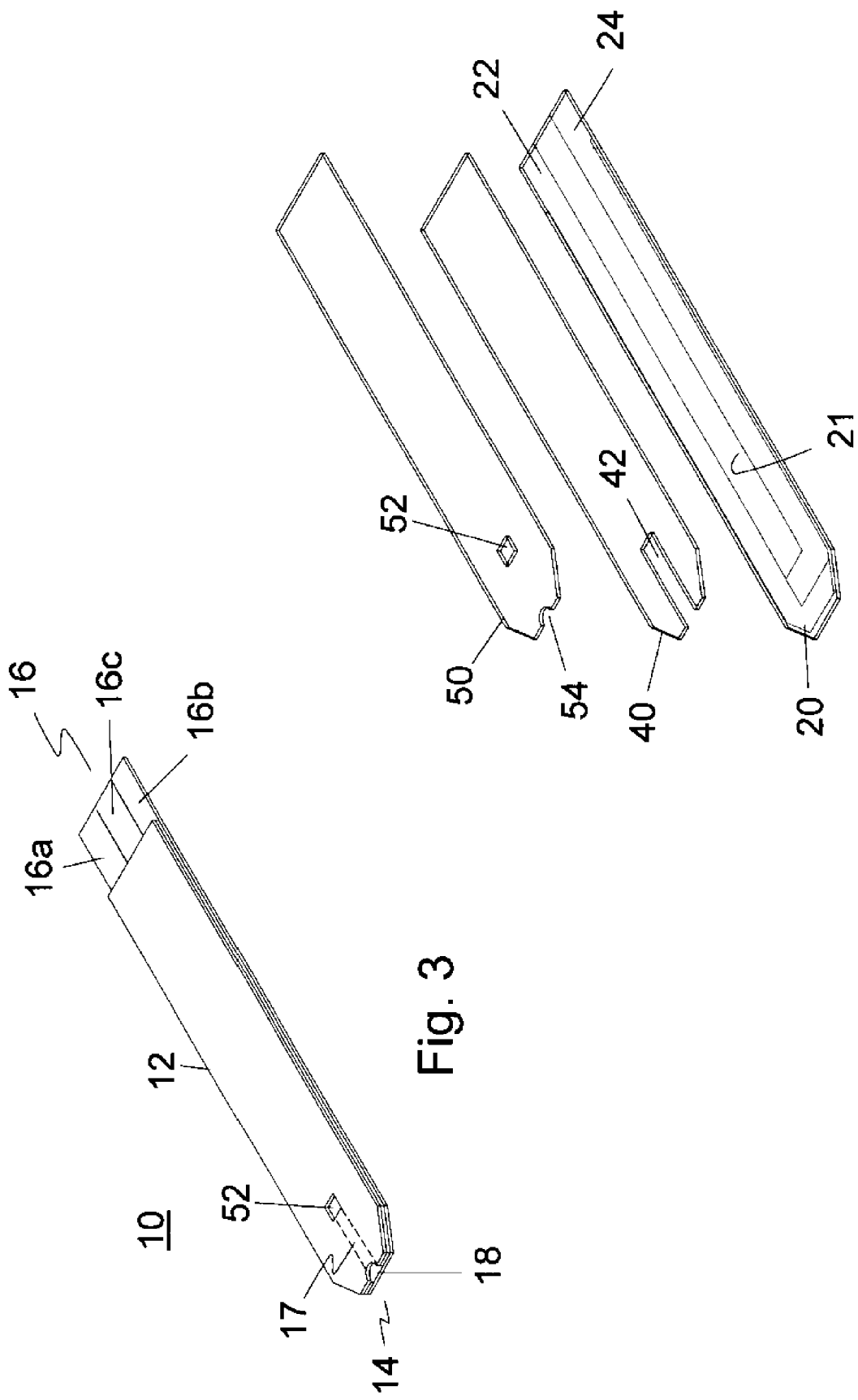

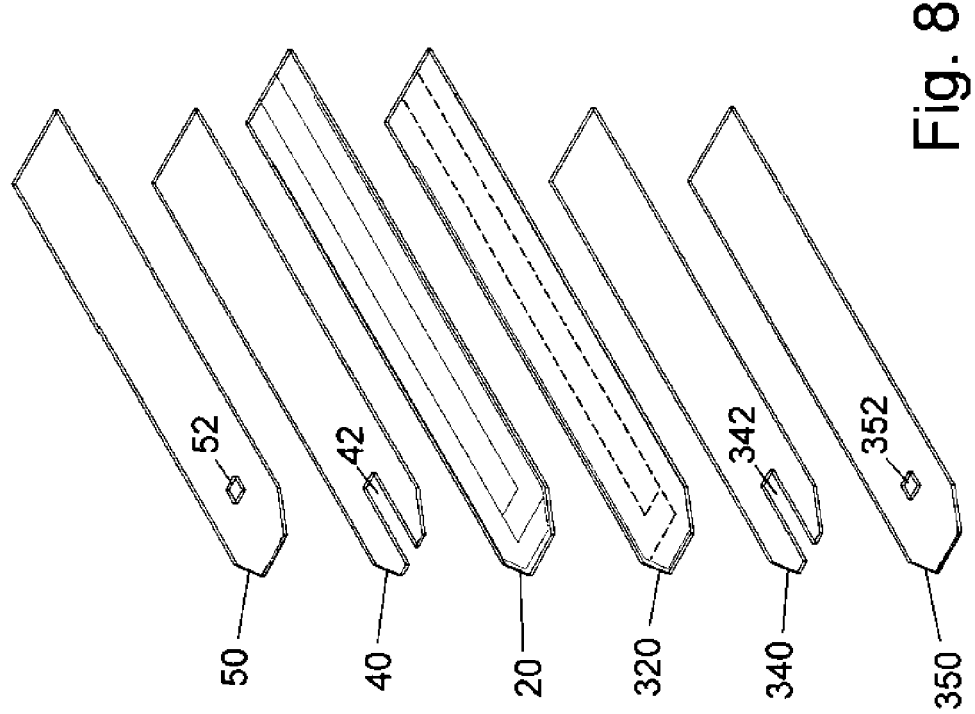
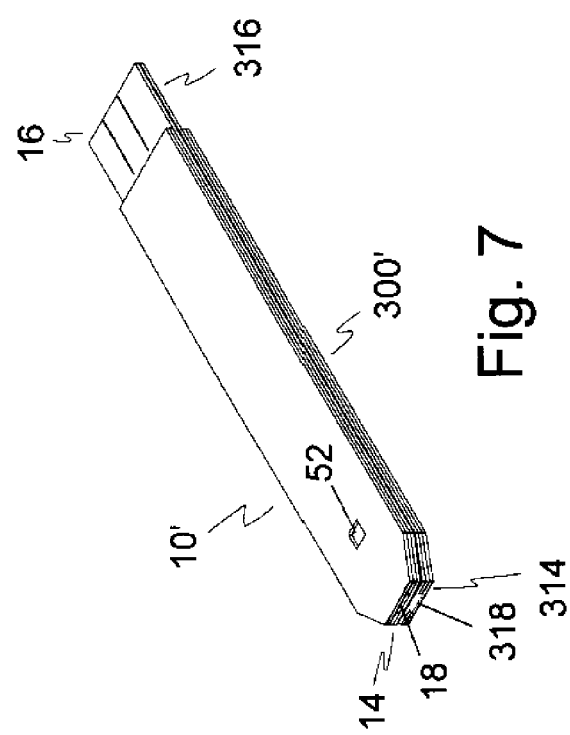

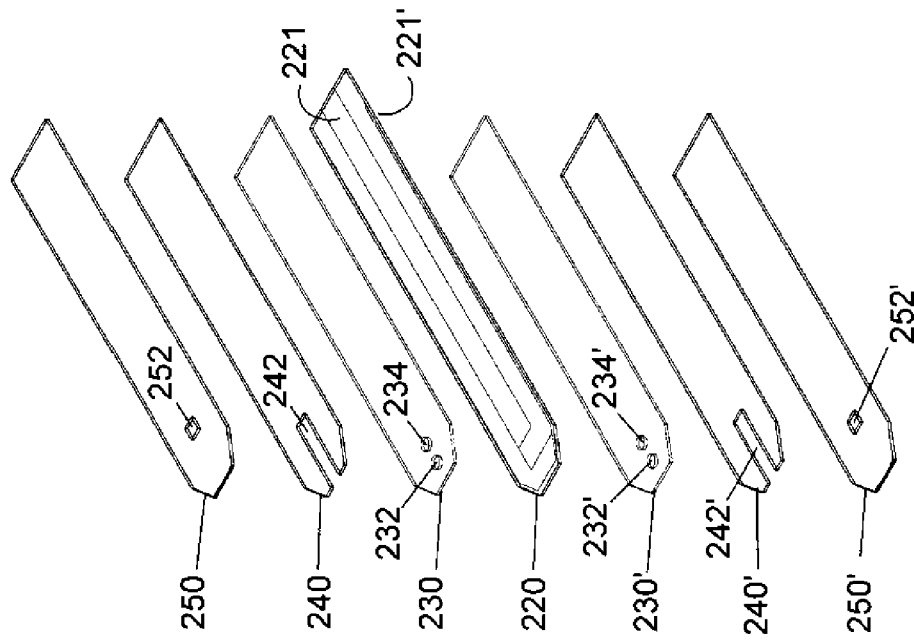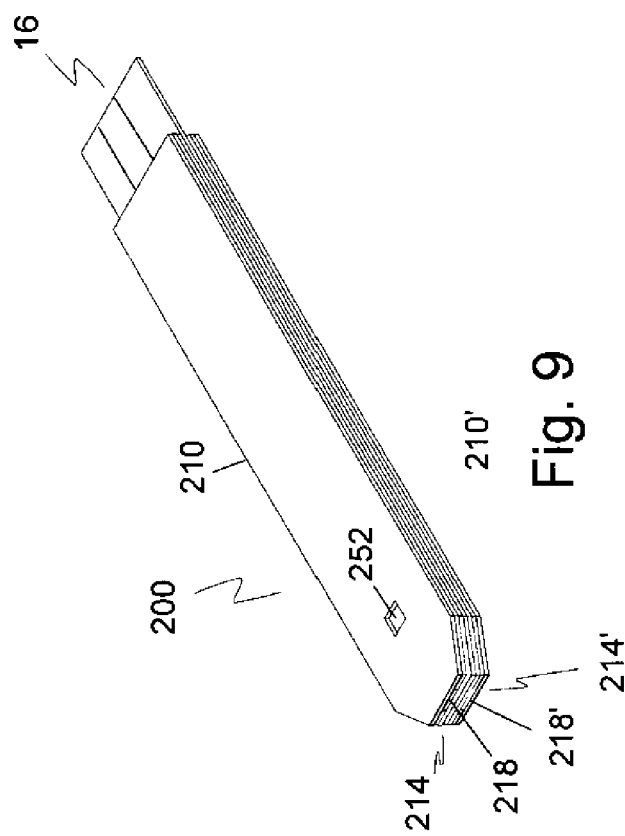
Fig. 9
Fig. 10

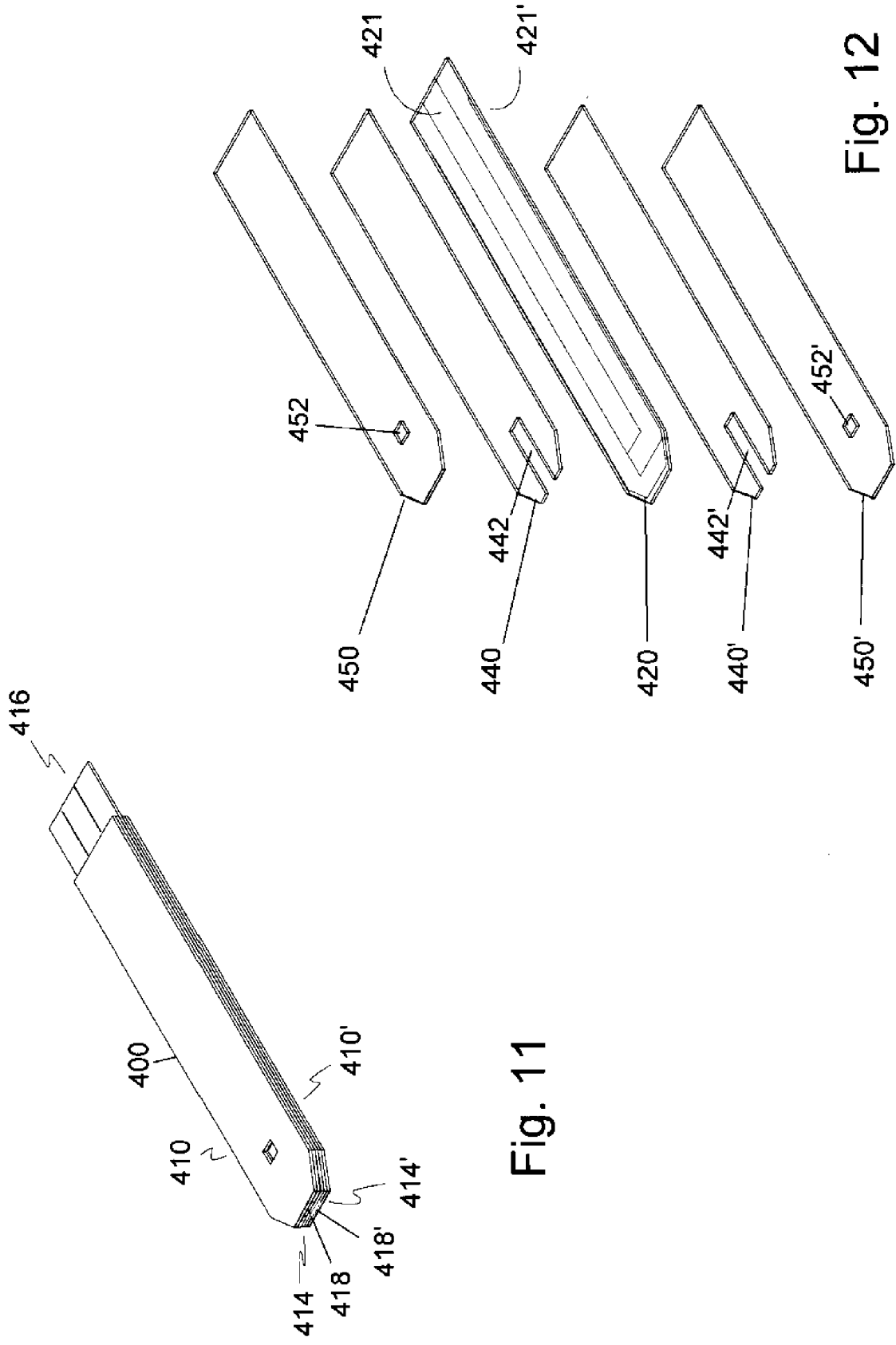

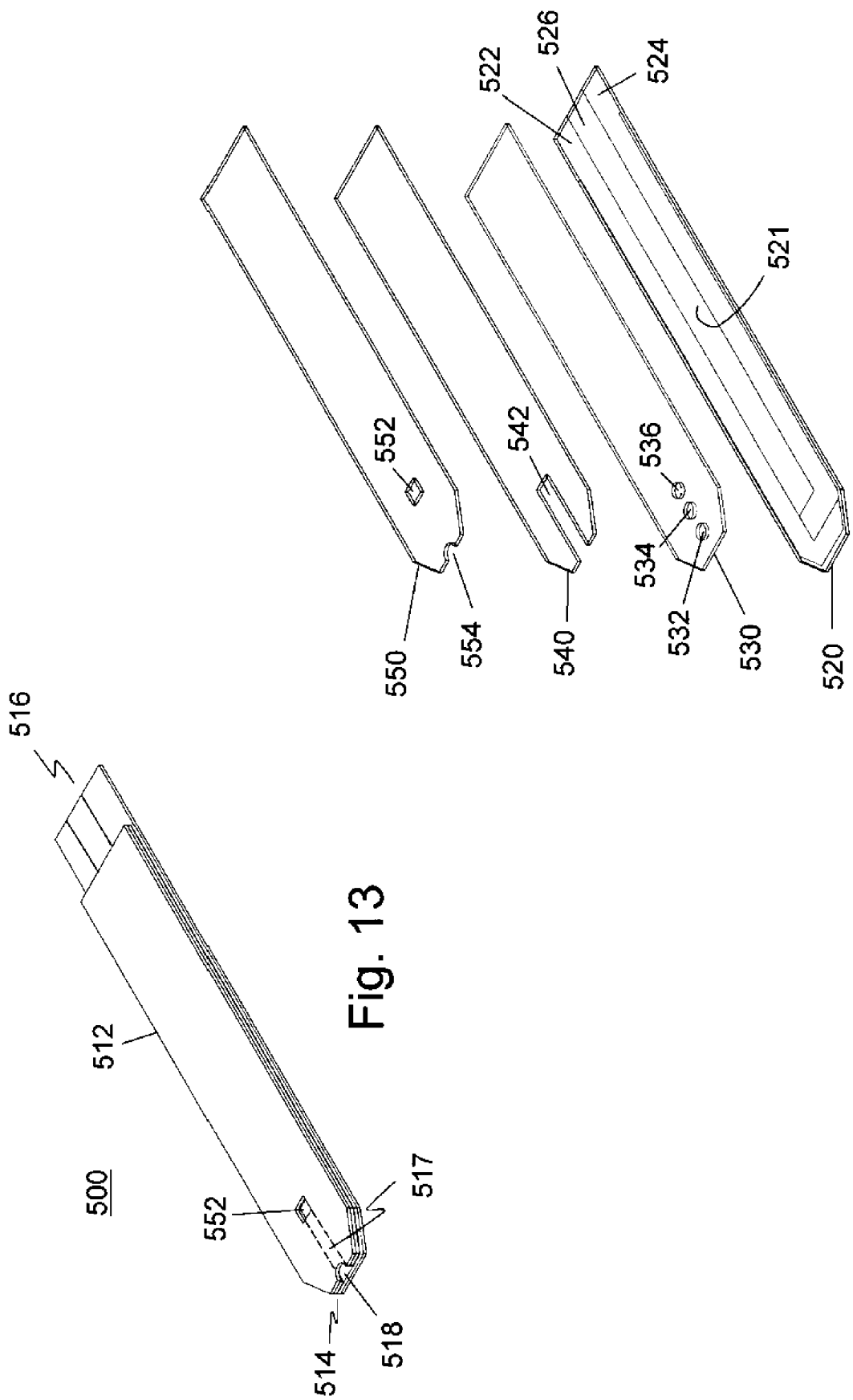

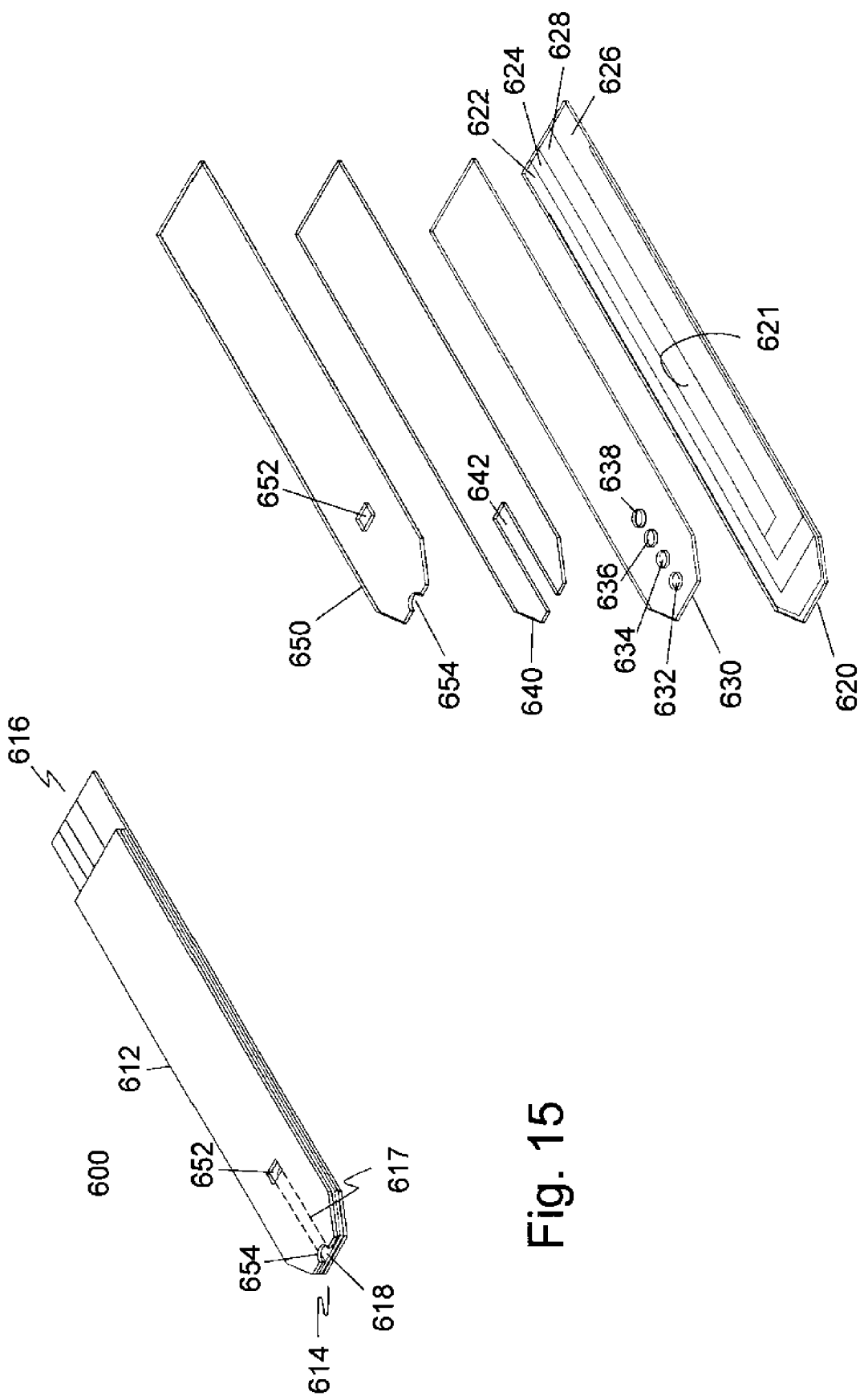

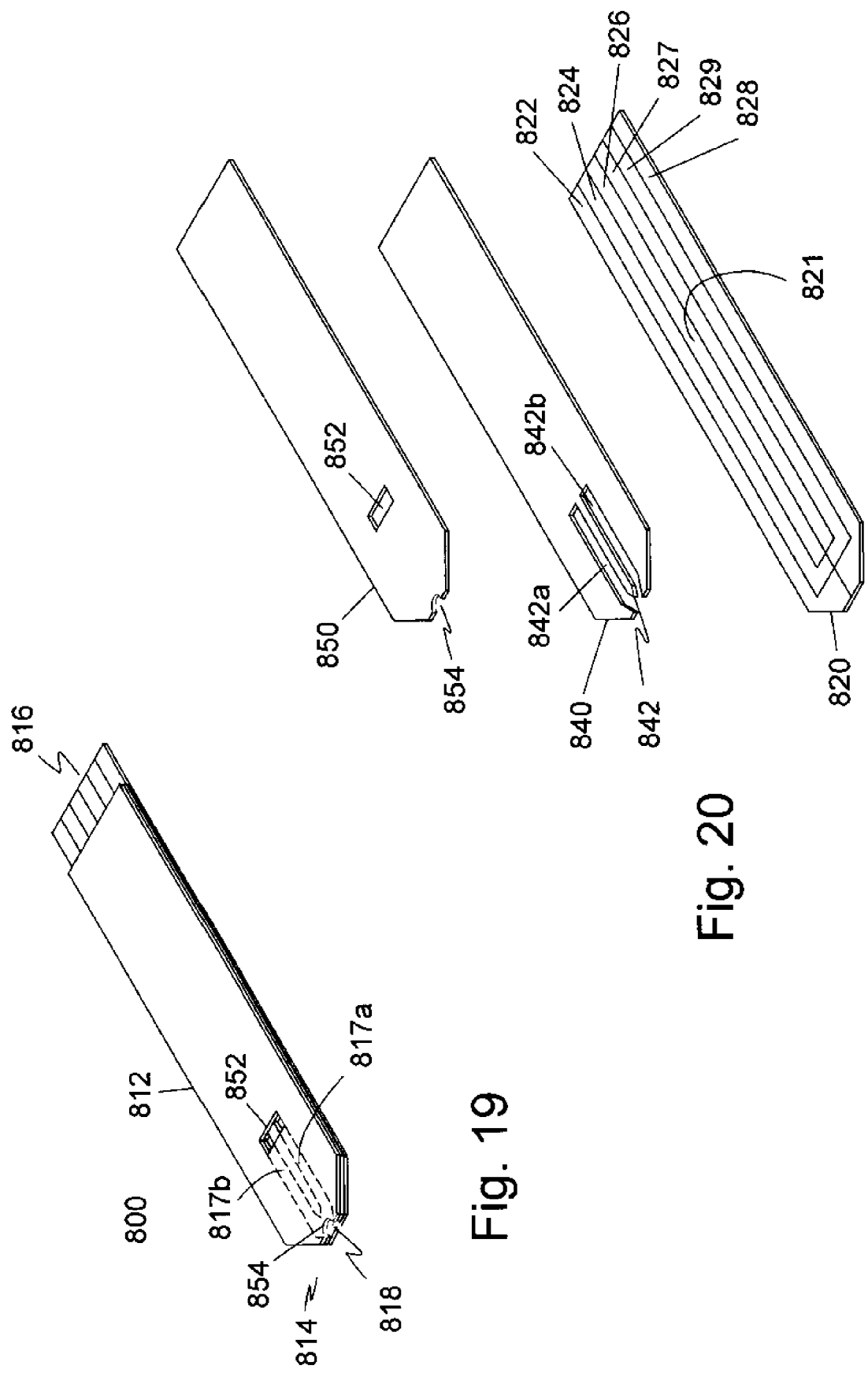

DISPOSABLE OXYGEN SENSOR AND METHOD FOR CORRECTING OXYGEN EFFECT ON OXIDASE-BASED ANALYTICAL DEVICES

BACKGROUND OF INVENTION

1. Field of the Invention

The present invention relates generally to an electrochemical sensor used for the quantification of a specific component or analyte in a liquid sample. Particularly, the present invention relates to an electrochemical sensor for the detection of analytes present in biological fluids. More particularly, the present invention relates to a disposable electrochemical sensor for the in vitro detection of oxygen concentration. Still more particularly, the present invention relates to a method of correcting of the oxygen effect on oxidase-based analytical devices.

2. Description of the Prior Art

The first generation of oxidase-based electrochemical biosensors used oxygen as the electron acceptor. Oxygen, however, becomes a limiting factor in the enzymatic reaction at high substrate concentrations due to the limited solubility of oxygen in liquid samples. This limits the upper linear range of the biosensors. In order to overcome problems associated with insufficient oxygen concentration, a second generation of biosensors was developed that used electron mediators as substitutes for oxygen. The electron mediators are redox chemicals capable of mediating the electron transfer in the regeneration of the enzyme to the active form. The linear range of the resulting biosensors was significantly improved.

Various redox mediators have been investigated towards the development of commercial products. Among them, potassium ferricyanide, osmium redox couples, and ferrocene derivatives are the most popular. Such sensor reagent improvements highlight a key to the marketability of this type of product such as, for example, disposable glucose measuring strips. Disposable glucose measuring strips are based on the use of glucose oxidase and potassium ferricyanide, osmium redox couples, or ferrocene derivatives.

Although the mediator/oxidase-based biosensors eliminate the dependence on the oxygen concentration for the extended linear range of the sensor, oxygen related drawbacks still exist. Mediators are not as efficient at shuttling electrons with the enzyme as is the oxygen molecule. In fact, any oxygen in the sample solution can effectively compete for the enzyme site. Measurements made with the mediator/oxidase-based biosensors show significantly lower results with increasing oxygen in the fluid samples. The inaccurate testing results caused by varying oxygen concentration were investigated by several groups. This becomes especially important when using the glucose strips for point-of-care glucose testing in patients with high or unpredictable blood oxygen levels.

Additionally, biological specimens contain widely varying oxygen levels. The typical oxygen partial pressure, $pO_2$, of a venous blood sample is about 32±7 mm Hg. In some cases, it can be as low as 20 mmHg and as high as 50 mm Hg. For a normal arterial sample and capillary sample, one can expect much higher oxygen levels of about 85±10 mm Hg. For patients who are in oxygen therapy, the level of arterial $pO_2$ can reach 200 mm Hg or higher. Thus, the mediator/oxidase-based biosensors are prone to giving inaccurate test results resulting from the different oxygen concentrations when they are used for the measurement of blood samples other than capillary blood. This becomes more serious when the substrate concentration is at a low concentration level (e.g. glucose concentration less than 70 mg/dL).

To obviate the interference resulting from the varying oxygen concentration or so-called "oxygen effect" described above using the mediator/oxidase-based biosensors, an oxygen-insensitive enzyme such as glucose dehydrogenase was used to replace the oxygen-sensitive oxidase such as glucose oxidase. Glucose dehydrogenase, whose coenzyme is pyrroloquinoline quinone, does not interact with oxygen. Therefore, the resultant glucose sensor is unaffected by variable oxygen concentration in the sample. A few products have been developed and marketed using this enzyme. These included Accu-Chek™ Comfort Curve® by Roche Diagnostics, IN, USA, Freestyle® by TheraSense, Alameda, Calif., USA, and Ascensia® by Bayer Health Care, Mishawaka, Ind., USA.

The use of glucose dehydrogenase does overcome the problems associated with the oxygen effect. Glucose dehydrogenase, however, has other problems. One problem is that it is not as specific as glucose oxidase. Glucose dehydrogenase not only reacts with glucose but also reacts with other sugars like galactose and maltose. Both galactose and maltose have a similar structure to glucose. Maltose is composed of two glucose units and galactose differs in structure from glucose only in the position of the hydroxyl group on carbon number 4. Severe interference can be expected. As a matter of fact, the glucose dehydrogenase-based biosensors are more sensitive to maltose and have no discrimination between glucose and galactose. If a glucose monitor or test strips use a glucose dehydrogenase pyrroloquinolinequinone method, a falsely high glucose reading may be obtained by the patients. For this reason, the Centers for Medicare & Medicaid Services and ESRD Networks were alerted by the Food and Drug Administration (FDA) on Apr. 18, 2003, to a concern with peritoneal dialysis patients' glucoses while on Icodextrin Extraneal dialysis solution and the effects of falsely elevated glucoses because of the interaction of maltose. A false high blood glucose reading could cause the patients to be given more insulin than needed. Getting more insulin than needed can lower a patient's blood sugar unnecessarily and can cause a serious reaction including, but not limited to, loss of consciousness.

Therefore, what is needed is an oxygen sensor that can be used to measure dissolved oxygen accurately and precisely with a minimum quantity of sample volume. What is also needed is an oxygen sensor that is disposable. What is further needed is a disposable oxygen sensor and a method of correcting the oxygen effect on oxidase-based analytical devices. What is still further needed is a system for correcting the oxygen effect on oxidase-based analytical devices.

SUMMARY OF INVENTION

It is an object of the present invention to provide an electrochemical oxygen sensor that measures dissolved oxygen accurately in a small amount of analyte. It is another object of the present invention to provide an amperometric oxygen sensor that measures dissolved oxygen accurately in a sample of analyte of about 0.5 μL or less. It is a further object of the present invention to provide an amperometric oxygen sensor that is easily manufactured. It is still another object of the present invention to provide an amperometric oxygen sensor that is disposable and that measures oxygen with high accuracy and precision. It is yet another object of the present invention to provide a method for correcting the oxygen effect on oxidase-based analytical devices. It is a further object of the present invention to provide a system for correcting the oxygen effect on oxidase-based analytical devices.

The present invention achieves these and other objectives by providing an oxygen sensor that incorporates several embodiments including, but not limited to, either a 4-layer construction or 3-layer construction as disclosed in U.S. Pat. No. 6,767,441, U.S. Pat. No. 6,287,451, U.S. Pat. No. 6,258,229, U.S. Pat. No. 6,837,976, and U.S. Patent Publication No. 2003/0196894A1, all of which are incorporated herein by reference.

The present invention has a laminated, elongated body having a sample fluid channel connected between a fluid sample inlet on one end of the laminated body and a vent hole spaced from the inlet. Within the fluid channel lie at least one working electrode and a reference electrode. The arrangement of the working electrode and the reference electrode is not important for purposes of the results obtained from the sensor. The working electrode and the reference electrode are each in electrical contact with separate conductive paths. The separate conductive paths terminate on the end opposite the open channel end of the laminated body and are exposed for making an electrical connection to a reading device.

The laminated body has a bottom layer made from a plastic material. In one embodiment, several conductive paths are delineated on one side of the bottom layer. The conductive paths may be deposited on the bottom layer by screen printing, by vapor deposition, or by any method that provides for a conductive coating that adheres to the bottom layer. The conductive paths may be individually disposed on the bottom layer, or a conductive coating may be disposed on the bottom layer followed by etching/scribing the required number of conductive paths. The etching process may be accomplished chemically, mechanically scribing lines in the conductive layer, using a laser to scribe the conductive layer into separate conductive paths, or by any means that will cause a break between and among the separate conductive paths required by the present invention. Conductive coatings that may be used are coatings of copper, gold, tin oxide/gold, palladium, other noble metals or their oxides, or carbon film compositions. The preferred conductive coatings are gold film or a tin oxide/gold film composition.

In one embodiment of the present invention (4-layer construction), the laminated body has a first middle layer, also called a reagent holding/electrode area defining layer, on top of the bottom layer and the conductive paths. The first middle layer, or reagent holding layer, contains at least two openings that form wells for one or more working electrodes and a reference electrode when laminated to the bottom layer. Each opening corresponds to and exposes a small portion of a single conductive path. The wells for hold a reagent matrix. When more than one working electrode is included, the openings for the working electrodes are substantially the same size. The opening for the reference electrode may be the same or different size as the openings for the working electrodes. The placement of all of the openings is such that they will be all positioned within the sample fluid channel described above. The reagent holding layer is also made of an insulating dielectric material, preferably plastic, and may be made by die cutting the material mechanically or with a laser and then adhering the material to the bottom layer. An adhesive, such as a pressure-sensitive adhesive, may be used to secure the reagent holding layer to the base layer. Adhesion may also be accomplished by ultrasonically bonding the reagent layer to the base layer. The reagent holding layer may also be made by screen printing an insulating material or by binding a photopolymer over the base layer.

The laminated body also has a second middle layer, also called a channel forming layer, on top of the reagent holding layer. The channel forming layer is also made of a plastic insulating material and creates the sample fluid channel of the laminated body. A U-shaped cutout is formed in one end of the channel forming layer which overlays the electrode wells in the reagent holding layer with the open end forming the fluid sample inlet of the laminated body described earlier. A double coated, pressure-sensitive adhesive tape may be used as the channel forming layer.

The laminated body of the present invention has a cover with a vent opening. The vent opening is located such that at least a portion of the vent opening overlays the bottom of the U-shaped cutout of the channel forming layer. The vent allows air within the sample fluid channel to escape as the fluid sample enters the sample inlet of the laminated body. The fluid sample generally fills the fluid sample channel by capillary action. In small volume situations, the extent of capillary action is dependent on the hydrophobic/hydrophilic nature of the surfaces in contact with the fluid undergoing capillary action. Capillary forces are enhanced by either using a hydrophilic material to form the cover, or by coating at least a portion of one side of a hydrophobic material with a hydrophilic substance in the area of the cover that faces the fluid sample channel between the sample inlet of the laminated body and the vent opening of the cover. It should be understood that an entire side of the cover may be coated with the hydrophilic substance and then bonded to the channel forming layer.

In the embodiments using a reagent holding layer (4-layer construction), one of the electrode wells contains electrode material (i.e. reagent matrix) for the working electrode (W) and one for the reference electrode (R). The positional arrangement of the working electrode and the reference electrode in the channel are not critical for obtaining usable results from the oxygen sensor. The possible electrode arrangements within the fluid sample channel may be W-R or R-W with the arrangement listed as the arrangement of electrodes would appear from the open end of the laminated body to the vent opening. The preferred position was found to be W-R; that is, as the sample fluid enters the sample inlet of the laminated body, the fluid sample covers W first, then R. The working electrode and the reference electrode are each in electrical contact with separate conductive paths, respectively. The separate conductive paths terminate and are exposed for making an electrical connection to a reading device on the end opposite the sample inlet end of the laminated body.

The working electrode is loaded with an oxygen measuring reagent or mixture containing at least a reduced form of redox mediator, an oxidase, and a peroxidase. The oxygen measuring reagent may optionally contain a surfactant, a polymer binder, an inactive bulking agent, and an antioxidant. The reference electrode may be loaded with the same mixture as the working electrode. It should be pointed out that the reference electrode well could be loaded with a redox mediator (either reduced or oxidized form or their mixture) with or without a surfactant, a polymer binder, an inactive bulking agent, and an antioxidant. The reference electrode well could also be loaded with a Ag/AgCl layer (e.g. by applying Ag/AgCl ink or by sputter-coating a Ag or Ag/AgCl layer) or other reference electrode materials.

In the 3-layer embodiment, the three layers are the same or similar to those in the 4-layer construction except that it does not include a reagent holding layer. The U-shaped channel cutout is located at the sensor end (sample inlet end). The length, width and thickness of the U-shaped channel cutout define the capillary channel volume. The length and width of the U-shaped channel cutout along with the base conductive layer define the areas of the working and reference electrodes. The working electrode (W) and reference electrode (R) are preferably covered by the same reagent mixture.

The redox mediator is capable of transferring electrons between the enzyme-catalyzed reactions and the working electrode. The preferable mediators are redox chemicals in reduced form. The mediator used in the present invention may be at least one of a variety of chemicals in their reduced form, or virtually any oxidizable species or electron donors. Examples of usable compounds are potassium ferrocyanide ($K_4Fe(CN)_6$), $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, various ferrocenes, methylene blue, methylene green, 7,7,8,8-tetracyanoquinodimethane (TCNQ), tetrathiafulvalene (TTF), toluidine blue, meldola blue, N-methylphenazine methosulfate, phenyldiamines, 3,3',5,5'-tetramethylbenzidine (TMB), pyrogallol, and benzoquinone (BQ) where phen is 1,10-phenanthroline and bpy is 2,2'-bipyridine. It is desirable that the mediator is capable of being oxidized chemically by hydrogen peroxide resulting from the enzymatic reactions such as those described in Eqs. (1) and (2) below. It is further desirable that the oxidation form of the mediator is capable of being reduced electrochemically at the working electrodes at the applied potential. It is still further desirable that the mediator is stable in the matrix. The preferred mediator in the present invention is potassium ferrocyanide.

The oxidase is selected from those capable of producing hydrogen peroxide, such as, for example, glucose oxidase (GOD), acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, xanthine oxidase, and the like. In the present invention, glucose oxidase is used.

The peroxidase may be from any source such as soybean (soybean peroxidase (SBP)) or horseradish root (horseradish root peroxidase (HRP)).

Surfactants may be selected from, but are not limited to, various anionic, cationic, non-ionic and zwitterionic detergents, such as Triton X-100, Tween 20, sodium cholate hydrate, hexadecylpyridinium cholide monohydrate, and CHAPs. The preferred surfactant in the present invention is Triton X-100.

Polymer binders may be selected from, but are not limited to, various water-soluble polymers, such as polyvinylpyrrolidone, polyethylene oxide, poly(vinyl alcohol), poly(ethylene glycol), poly(propylene glycol), polysulfone, carboxy methyl cellulose, hydroxypropyl cellulose, methyl cellulose, poly(2-ethyl-2oxazoline), and the like. The preferred polymers in the present invention are polyethylene oxide (PEO) and methylcellulose. The molecular weight of PEO is in the range from thousands to millions. The preferred PEO molecular weight is over 1 million, and, more preferably, it is about 4 million.

Antioxidants may be selected from, but are not limited to, various reductants and oxygen scavengers such as, for example, sodium sulfite, sodium hydrosulfite, hydrazine, hydroquinone, carbohydrazide, N,N-Diethylhydroxylamine, methylethylketoxime, diethylthreitol, erythorbic acid, and ascorbic acid. The preferred antioxidant in the present invention is sodium sulfite.

Bulking agents can be any compounds that do not react with any of the other ingredients within the reagent matrix and are inactive with the electrode surface. One class of bulking agents that meets these requirements are compounds such as sugars. Sugars can be selected from, but are not limited to, inactive sugars (i.e. not reacting with the enzymes or other ingredients used in the reagent mixture, not active at the electrode surface), such as trehalose, galactose, suctose, lactose, mannitol, mannose, fructose, sucrose, lactose, lactitol, sorbitol, and xylitol, maltose, and the like. The preferred bulking agent in the present invention is D(+)-trehalose.

In the working electrode well, glucose in a sample is oxidized in the presence of GOD by dissolved oxygen when the sample enters the channel. The resulting products include gluconic acid and hydrogen oxide. The reaction equation is given below:

$$\text{Glucose} + O_2 \rightarrow \text{Gluconic acid} + H_2O_2 \quad (1)$$

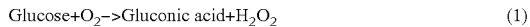

The reduced form of ferrocyanide mediator, $[Fe(CN)_6]^{4-}$, is capable of being oxidized to ferricyanide, $[Fe(CN)_6]^{3-}$ in the presence of a peroxidase by hydrogen peroxide resulting from the above enzymatic reaction. When using ferrocyanide as the mediator, the oxidation reaction is as shown below:

$$[Fe(CN)_6]^{4-} + H_2O_2 \rightarrow [Fe(CN)_6]^{3-} + H_2O \quad (2)$$

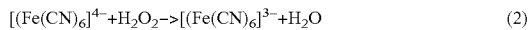

The oxidized form of the ferrocyanide ion (i.e. ferricyanide, $[Fe(CN)_6]^{3-}$), is capable of being reduced electrochemically when an appropriate potential is applied to the working electrode. The resulting current signal is related to the glucose concentration as well as the oxygen concentration. Furthermore, if the glucose concentration is known, the oxygen concentration or $pO_2$ can be calculated. It is also desirable to use a potential where the electro-oxidation of other oxidizable interferents like ascorbic acid and acetaminophen either does not occur or is minimal. An example of such an applied potential is between about 0.0 V and about −0.6 V as measured against the reference electrode of the present invention. The preferred potential is about −0.3 V. This potential is preferred for providing a good ratio of signal versus background noise/interference.

In another embodiment of the present invention, it is preferred to combine the oxygen sensor of the current invention with a glucose strip into one dual-strip such that the oxygen concentration can be measured and calculated substantially simultaneously with glucose, using one drop or less of liquid sample. Once the correlation between the oxygen concentration and the oxygen effect on the glucose strip is known, the glucose concentration can be corrected for the oxygen effect when used for the measurement of samples with varying amounts of oxygen.

The embodiment of the combined sensor includes various configurations including, but not limited to, a dual-strip configuration that is arranged in a back-to-back format, or side-by-side format. Another configuration includes a bottom layer that has a conductive coating on both sides. The bottom layer would be assembled on one side as an oxygen sensor and on the other side as an oxidase-based analyte sensor that would effectively make the bottom layer a middle layer to the entire strip combination assembly. In yet, another embodiment, the combined sensor includes two working electrodes, one as the oxygen working electrode and the other as the oxidase-based analyte working electrode, and a reference electrode. In still another embodiment, the combined sensor includes three working electrodes (e.g. an oxygen electrode, an oxidase-based analyte electrode, and an interference eliminating electrode) and at least one reference electrode.

It should be noted that other oxidase-based sensors can be combined with the oxygen sensors of the present invention.

All of the advantages of the present invention will be made clearer upon review of the detailed description, drawings and appended claims.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 3 is a perspective view of another embodiment of the present invention showing the test strip.

FIG. 4 is an exploded view of the embodiment in FIG. 3 showing the three component layers of the test strip.

FIG. 7 is a perspective view of another embodiment of the present invention showing the combination of a three-layer oxygen sensor strip and a three-layer oxidase-based analyte sensor strip.

FIG. 8 is an exploded view of the embodiment in FIG. 7 showing the arrangement of the component layers of the oxygen sensor strip and the oxidase-based analyte sensor strip.

FIG. 9 is a perspective view of another embodiment of the present invention showing the combination of a four-layer oxygen sensor strip and a four-layer oxidase-based analyte sensor strip where the base layer is common to both sensors.

FIG. 10 is an exploded view of the embodiment in FIG. 9 showing the arrangement of the component layers of the oxygen sensor and the oxidase-based analyte sensor.

FIG. 11 is a perspective view of another embodiment of the present invention showing the combination of a three-layer oxygen sensor strip and a three-layer oxidase-based analyte sensor strip where the base layer is common to both sensors.

FIG. 12 is an exploded view of the embodiment in FIG. 11 showing the arrangement of the component layers of the oxygen sensor and the oxidase-based analyte sensor.

FIG. 13 is a perspective view of another embodiment of the present invention showing a combined sensor strip having the four layer construction with two working electrodes namely, an oxygen electrode and an oxidase-based analyte electrode.

FIG. 14 is an exploded view of the embodiment in FIG. 13 showing the arrangement of the component layers that includes an oxygen electrode, an oxidase-based analyte electrode and a reference electrode.

FIG. 15 is a perspective view of another embodiment of the present invention showing a combined sensor strip having the four-layer construction with three working electrodes namely, an oxygen electrode, an oxidase-based analyte electrode and an interferant-compensating electrode.

FIG. 16 is an exploded view of the embodiment in FIG. 15 showing the arrangement of the component layers that includes an oxygen electrode, an oxidase-based analyte electrode, an interferent-compensating electrode, and a reference electrode.

FIG. 19 is a perspective view of another embodiment of the present invention showing a combined sensor strip having the three-layer construction with an oxygen sensor system side-by-side with an oxidase-based analyte electrode.

FIG. 20 is an exploded view of the embodiment in FIG. 19 showing the arrangement of the component layers that includes the oxygen electrode system and the oxidase-based analyte electrode system.

DETAILED DESCRIPTION OF THE PREFERRED EMBODIMENT

Figure 6:
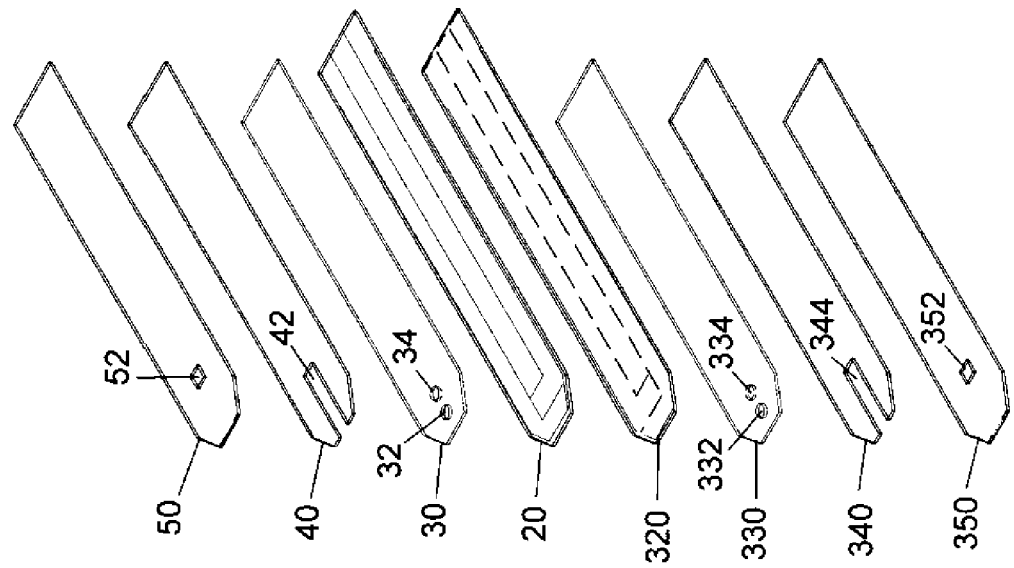
FIG. 6 is an exploded view of the embodiment in FIG. 5 showing the arrangement of the component layers of the oxygen sensor strip and the oxidase-based analyte sensor strip.

The preferred embodiments of the present invention are illustrated in FIGS. 1-26. The oxygen sensor of the present invention can be made using either a 4-layer construction (FIG. 1) or a 3-layer construction (FIG. 3). The 4-layer construction has the same three layers as the 3-layer construction and an additional reagent holding layer between a base/bottom layer and a channel forming layer.

Turning now to FIG. 1, the oxygen sensor 10 has a laminated body 12, a fluid sampling end 14, an electrical contact end 16, and a vent opening 52. Fluid sampling end 14 includes a fluid sample channel 17 between a sampling end inlet 18 and vent opening 52. Electrical contact end 16 has three discrete conductive contacts 16a, 16b and 16c.

Turning now to FIG. 2, laminated body 12 is composed of a bottom layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Bottom layer 20 has a conductive layer 21 on which is delineated to at least two conductive paths 22 and 24. The conductive paths 22, 24 may be formed by scribing or scoring conductive layer 21, or by silk-screening conductive paths 22, 24 onto bottom layer 20. Bottom layer 20 may also have a third conductive path 26 for incorporating another working electrode or other sensor combination that will be described later. Scribing or scoring of conductive layer 21 may be done by mechanically scribing the conductive layer 21 sufficiently to create at least two independent conductive paths 22, 24. The preferred scribing or scoring method of the present invention is done by using a carbon dioxide laser, a YAG laser or an eximer laser. Conductive layer 21 may be made of any electrically conductive material such as, for example, copper, gold, tin oxide/gold, palladium, other noble metals or their oxides, or carbon film compositions. The preferred electrically conductive material is gold or tin oxide/gold. A usable material for base layer 20 is a tin oxide/gold polyester film (Cat. No. FM-1) or a gold polyester film (Cat. No. FM-2) sold by Courtaulds Performance Films, Canoga Park, Calif.

In the embodiments using a reagent holding layer 30 (4-layer construction), reagent holding layer 30 has at least two reagent holding openings 32 and 34. Reagent holding opening 32 exposes a portion of conductive path 22 and reagent holding opening 34 exposes a portion of conductive path 24 creating reagent holding wells. Reagent holding layer 30 is made of a plastic material, preferably a medical grade one-sided adhesive tape available from Adhesive Research, Inc., of Glen Rock, Pa. Acceptable thicknesses of the tape for use in the present invention are in the range of about 0.001 in. (0.025 mm) to about 0.005 in. (0.13 mm). One such tape, Arcare® 7815 (about 0.003 in. (0.075 mm)), is preferred due to its ease of handling and good performance in terms of its ability to hold a sufficient quantity of chemical reagents and to promote capillary action through the fluid sample channel of the sensor. It should be understood that the use of a tape is not required. Reagent holding layer 30 may be made from a plastic sheet and may be coated with a pressure sensitive adhesive, a photopolymer, ultrasonically-bonded to base layer 20, or silk-screened onto the base layer 20 to achieve the same results as using the polyester tape mentioned.

The two reagent holding openings 32, 34 define electrode areas W and R, respectively, and hold chemical reagents forming one working electrode and one reference electrode. Generally, electrode area W is loaded with an oxygen reagent matrix that contains an oxidase, a redox mediator (preferably a reduced form of the redox mediator) and a peroxidase. One or more chemical components such as polymers, surfactants, bulking agents, and antioxidants may be optionally included in the oxygen reagent matrix. A reference reagent matrix may be loaded in electrode area R that is similar to the oxygen reagent matrix.

Typically, electrode area R must be loaded with a redox reagent or mediator to make the reference electrode function when using the preferred conductive coating material. If R is not loaded with a redox reagent or mediator, working electrode W will not function properly. The reference electrode (electrode area R) could be also loaded with a Ag/AgCl layer (e.g. by applying Ag/AgCl ink or by sputter-coating a Ag or Ag/AgCl layer) or other reference electrode materials that do not require a redox mediator to function properly.

The size of the reagent holding openings is preferred to be made as small as possible in order to make the fluid sample channel of the oxygen sensor as short as possible while still being capable of holding sufficient chemical reagent to function properly. The preferred shape of the reagent holding openings is round and has a preferred diameter of about 0.03 in. (0.76 mm). The two reagent holding openings 32, 34 are aligned with each other and are spaced about 0.0256 in. (0.65 mm) from each other. The circular reagent holding openings are for illustrative purposes only. It should be understood that the shape of the reagent holding openings is not critical provided that the size of the openings is big enough to facilitate dispensing chemical reagents but small enough to allow for a reasonably small sample channel.

The positional arrangement of the working electrode and the reference electrode in the channel is not critical for obtaining usable results from the oxygen sensor. The possible electrode arrangements within the sample fluid channel may be W-R or R-W, with the arrangement listed as the arrangement of electrodes would appear from the sample inlet 18 of laminated body 12 to the vent opening 52. The preferred position was found to be W-R; that is, as the fluid sample enters sampling end 14 of laminated body 12, the fluid sample would cover W first, then R. Such an arrangement may be beneficial for obtaining usable results when the sample is insufficient or partially insufficient.

The working electrode and the reference electrode are each in electric contact with separate conductive paths. The separate conductive paths terminate and are exposed for making an electric connection to a reading device on the end opposite the sample inlet 18 of laminated body 12.

In the embodiments using reagent holding layer 30 (4-layer construction), channel forming layer 40 has a U-shaped cutout 42 located at the fluid sampling end 14. The length of cutout 42 is such that when channel forming layer 40 is laminated to reagent holding layer 30, electrode areas W and R are within the space defined by cutout 42. The length, width and thickness of the U-shaped cutout 42 define the capillary channel volume. The thickness of channel forming layer 40 can affect the speed of the sample fluid flow into the fluid sample channel, which is filled by capillary action of the sample fluid. Channel forming layer 40 is made of a plastic material, preferably a medical grade double-sided pressure sensitive adhesive tape available from Adhesive Research, Inc., of Glen Rock, Pa. Acceptable thicknesses of the tape for use in the present invention are in the range of about 0.001 in. (0.025 mm) to about 0.010 in. (0.25 mm). One such tape is Arcare® 7840 (about 0.0035 in. (0.089 mm)). U-shaped cutout 42 can be made with a laser or by die-cutting. The preferred method is to die-cut the cutout. The preferred size of the U-shaped cutout is about 0.155 in. long (3.94 mm), about 0.05 in. wide (1.27 mm) and about 0.0035 in. thick (0.089 mm).

Cover 50, which is laminated to channel forming layer 40, has vent opening 52 spaced from the fluid sampling end 14 of oxygen sensor 10 to insure that fluid sample in the fluid channel 17 will completely cover electrode areas W and R. Vent opening 52 is positioned in cover 50 so that it will align somewhat with U-shaped cutout 42. Preferably, vent opening 52 will expose a portion of and partially overlay the bottom of the U-shaped cutout 42. The preferable shape of vent hole 52 is a rectangle with dimensions of about 0.08 in. (2 mm) by about 0.035 in. (0.9 mm). The preferred material for cover 50 is a polyester film. In order to facilitate the capillary action, it is desirable for the polyester film to have a highly hydrophilic surface that faces the capillary channel. Transparency films (Cat. No. PP2200 or PP2500) from 3M are the preferred material used as the cover in the present invention.

FIG. 3 illustrates a 3-layer oxygen sensor 10'. Like the 4-layer embodiment, oxygen sensor 10' has a laminated body 12, a fluid sampling end 14, an electrical contact end 16, and a vent opening 52. Fluid sampling end 14 includes a fluid sample channel 17 between a sampling end inlet 18 and vent opening 52. Electrical contact end 16 has three discrete conductive contacts 16a, 16b and 16c.

As can be seen from FIG. 4, laminated body 12 is composed of a bottom layer 20, a channel forming layer 40, and a cover 50. As noted earlier, all layers of laminated body 12 are made of a dielectric material, preferably plastic. Unlike the 4-layer embodiment, there is no separate reagent holding layer in the 3-layer embodiment. Channel forming layer 40 also delineates the area in which a pre-determined amount of reagent matrix is disposed.

Figure 5:
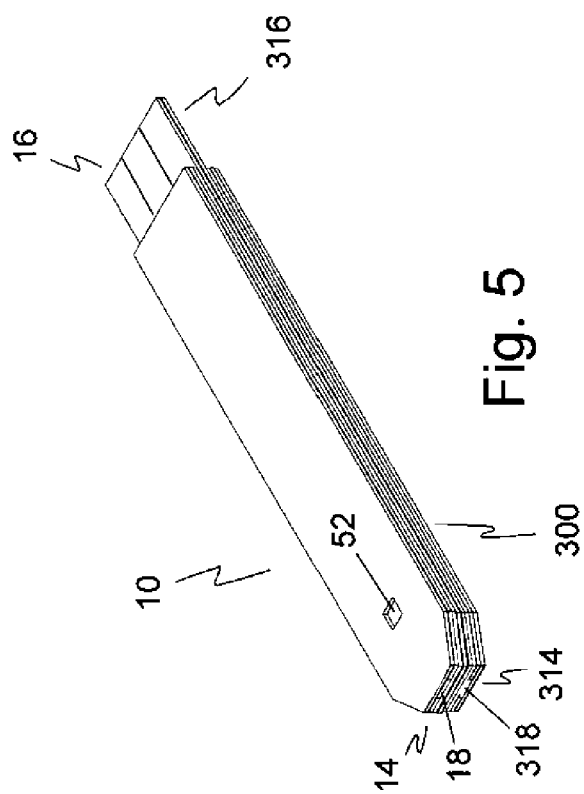
FIG. 5 is a perspective view of another embodiment of the present invention showing the combination of a four-layer oxygen sensor strip and a four-layer oxidase-based analyte sensor strip.

FIG. 5 shows a combination of an oxygen sensor 10 and an oxidase-base sensor 300. Both oxygen sensor 10 and oxidase-based sensor 300 are made of the 4-layer construction where the bottoms of each sensor are laminated to each other forming an integrated oxygen/oxidase-based analyte sensor combination. Each sensor has a laminated body 12, 312, a fluid sampling end 14, 314, an electrical contact end 16, 316, and a vent opening 52, 352 (not shown). Fluid sampling ends 14, 314 include sample fluid channels (not shown) between sampling end inlets 18, 318 and vent openings 52, 352, respectively.

Turning now to FIG. 6, each sensor 10, 300 has a bottom layer 20, 320, a reagent holding layer 30, 330, a channel forming layer 40, 340, and a cover 50, 350. Reagent holding layers 30, 330 have reagent holding openings 32, 34 and 332, 334, respectively. Channel forming layers 40, 340 have U-shaped cutouts 42, 342, respectively. Typically, an adhesive is used to hold sensors 10 and 300 together. Preferably, an additional layer with adhesive on both sides is used to facilitate assembly of sensor 10 to sensor 300.

FIG. 7 shows another combination embodiment of an oxygen sensor 10' and an oxidase-based analyte sensor 300'. Both oxygen sensor 10' and oxidase-based analyte sensor 300' are made of the 3-layer construction where the bottoms of each sensor are laminated to each other forming an integrated oxygen/oxidase-based analyte sensor combination. Each sensor has a laminated body 12, 312, a fluid sampling end 14, 314, an electrical contact end 16, 316, and a vent opening 52, 352 (not shown). Fluid sampling ends 14, 314 include sample fluid channels (not shown) between sampling end inlets 18, 318 and vent openings 52, 352, respectively.

Turning now to FIG. 8, each sensor 10', 300' has a bottom layer 20, 320, a channel forming layer 40, 340, and a cover 50, 350. Channel forming layers 40, 340 have U-shaped cutouts 42, 342, respectively.

FIG. 9 illustrates an oxygen and an oxidase-based analyte sensor combination with a 7-layer laminated body 200. The combination includes an oxygen sensor 210 and an oxidase-based analyte sensor 210'. Laminated body 200 includes a fluid sampling end 214, an electrical contact end 216 and vent openings 252, 252' (not shown). Fluid sampling end 14 includes two sample fluid channels (not shown); one between sampling end inlet 218 and vent opening 252 and the other between sampling end inlet 218' and vent opening 252' (not shown).

FIG. 10 shows an expanded view of laminated body 200 of the embodiment in FIG. 9. Laminated body 200 has a central, bottom layer 220 with a conductive coating 221, 221' on each side delineating the conductive paths for the working and reference electrodes of each sensor. Each side of central, bottom layer 220 includes a reagent holding layer 230, 230', a channel forming layer 240, 240', and a cover 250, 250'. Reagent holding layers 230, 230' have reagent holding openings 232, 234 and 232', 234', respectively. Channel forming layers 240, 240' have U-shaped cutouts 242, 242', respectively.

FIG. 11 illustrates an oxygen sensor and an oxidase-based analyte sensor combination with a 5-layer laminated body 400. The combination includes an oxygen sensor 410 and an oxidased sensor 410'. Laminated body 400 includes a fluid sampling end 414, an electrical contact end 416 and vent openings 452, 452' (not shown). Fluid sampling end 414 includes two sample fluid channels (not shown); one between sampling end inlet 418 and vent opening 452 and the other between sampling end inlet 418' and vent opening 452' (not shown).

FIG. 12 shows an expanded view of laminated body 400 of the embodiment in FIG. 11. Laminated body 400 has a central, bottom layer 420 with a conductive coating 421, 421' on each side delineating the conductive paths for the working and reference electrodes of each sensor. Each side of central, bottom layer 420 includes a channel forming layer 440, 440' and a cover 450, 450'. Channel forming layers 440, 440' have U-shaped cutouts 442, 442', respectively.

It should be noted that, in any of the combination sensor systems, the inlet notch may be incorporated into the base layers and the reagent holding layers to facilitate loading of a portion of the fluid sample in each of the sample fluid channels of the oxygen and the oxidase-based analyte sensors.

Another embodiment of the combination sensor is illustrated in FIGS. 13 and 14. FIG. 13 shows a combination oxygen/oxidase-based analyte sensor 500 with a laminated body 512, a fluid sampling end 514, an electrical contact end 516 and a vent opening 552. One such example includes, but is not limited to, a combination oxygen and glucose sensor. Fluid sampling end 514 includes a sample fluid channel 517 between sample inlet 518 and vent opening 552.

FIG. 14 shows an expanded view of laminated body 512 of the embodiment in FIG. 13. Laminated body 512 has a bottom layer 520, a reagent holding layer 530, a channel forming layer 540, and a cover 550. Bottom layer 520 has a conductive layer 521 on which is delineated at least three conductive paths 522, 524 and 526. Reagent holding layer 530 has at least three reagent holding openings 532, 534 and 536. Reagent holding opening 532 exposes a portion of conductive path 522, reagent holding opening 534 exposes a portion of conductive path 524 and reagent holding opening 536 exposes a portion of conductive path 526, all creating respective electrode wells.

The three reagent holding openings 532, 534 and 536 define electrode areas W1, W2 and R, respectively, and hold chemical reagents forming a first working electrode, a second working electrode and one reference electrode. Generally, electrode area W1 is loaded with an oxygen reagent matrix that includes an oxidase, a reduced form of the redox mediator and a peroxidase. Electrode area W2 is loaded with an oxidase-based analyte reagent that includes an enzyme capable of catalyzing a reaction involving a substrate (the analyte) for the enzyme and a redox mediator (preferably an oxidized form of the redox mediator). A reference reagent matrix may be loaded in electrode area R that is similar to the oxygen reagent matrix or the oxidase-based analyte reagent matrix. The reference reagent matrix may be either the oxygen reagent matrix or the oxidase-base analyte reagent matrix without the enzyme. It should be noted that the positional arrangement of the two working electrodes and the reference electrode in the channel are not critical for obtaining usable results from the oxygen correcting sensor combination.

Typically, electrode area R must be loaded with a reference reagent such as, for example, a redox couple, a redox reagent or mediator, a Ag/AgCl layer (e.g. by applying Ag/AgCl ink or by sputter-coating a Ag or Ag/AgCl layer), or other reference electrode materials.

FIG. 15 illustrates yet another embodiment of the present invention showing a combination oxygen/oxidase-based analyte sensor with intereferant correction. FIG. 15 shows a combination oxygen/oxidase-based analyte sensor 600 with a laminated body 612, a fluid sampling end 614, an electrical contact end 616 and a vent opening 652. Sensor 600 may also include an optional inlet notch 654. Fluid sampling end 614 includes a fluid sample channel 617 between sample inlet 618 and vent opening 652.

FIG. 16 shows an expanded view of laminated body 612 of the embodiment in FIG. 15. Laminated body 612 has a bottom layer 620, a reagent holding layer 630, a channel forming layer 640 with a U-shaped cutout 642, and a cover 650 with an optional inlet notch 654. Bottom layer 620 has a conductive layer 621 on which is delineated to at least four conductive paths 622, 624, 626, and 628. Reagent holding layer 630 has at least four reagent holding openings 632, 634, 636, and 638. Reagent holding opening 632 exposes a portion of conductive path 622, reagent holding opening 634 exposes a portion of conductive path 624, reagent holding opening 636 exposes a portion of conductive path 626, and reagent holding opening 638 exposes a portion of conductive path 628; all forming respective electrode wells.

The four reagent holding openings 632, 634, 636, and 638 define electrode areas W1, W2, W3, and R, respectively, and hold chemical reagents forming a first working electrode, a second working electrode, a third working electrode, and one reference electrode. Generally, electrode area W3 is loaded with an oxygen reagent matrix that includes an oxidase, a redox mediator (preferably a reduced form of the redox mediator) and a peroxidase. Electrode area W2 is loaded with an oxidase-based analyte reagent that includes an enzyme capable of catalyzing a reaction involving a substrate (the analyte) for the enzyme and a redox mediator (preferably an oxidized form of the redox mediator). A reference reagent matrix may be loaded in both electrode area W3 and electrode area R that is similar to the oxygen reagent matrix or the oxidase-based analyte reagent matrix. In addition, the reference reagent matrix may be either the oxygen reagent matrix or the oxidase-base analyte reagent matrix without the enzyme.

Typically, electrode areas W1 and R must be loaded with a reference reagent such as, for example, a redox couple, a redox reagent. Electrode area R may, in the alternative, be loaded with a Ag/AgCl layer (e.g. by applying Ag/AgCl ink or by sputter-coating a Ag or Ag/AgCl layer) or other reference electrode materials.

Figures 17, 18:
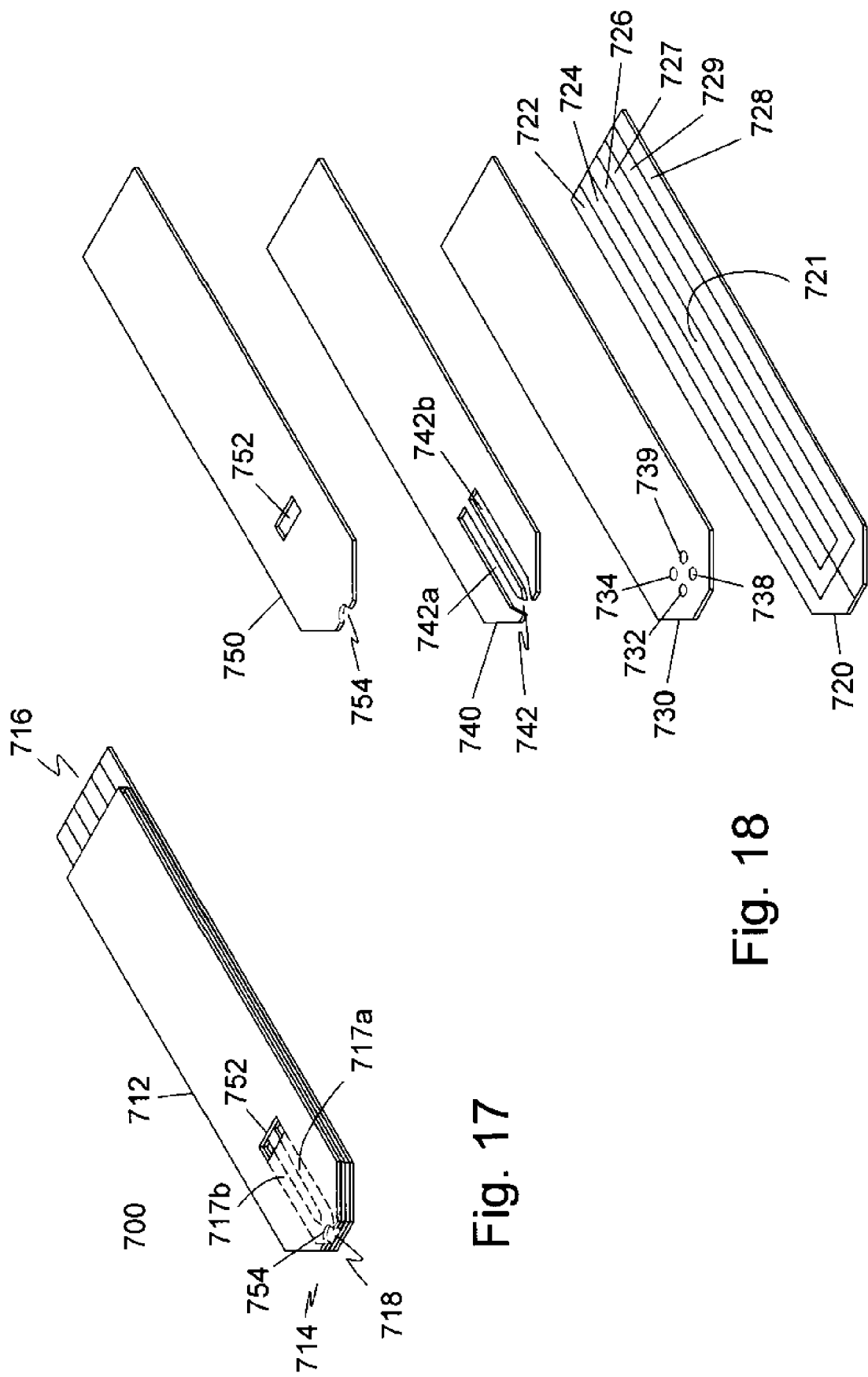
FIG. 17 is a perspective view of another embodiment of the present invention showing a combined sensor strip having the four-layer construction with an oxygen sensor system side-by-side with an oxidase-based analyte electrode.
FIG. 18 is an exploded view of the embodiment in FIG. 17 showing the arrangement of the component layers that includes the oxygen electrode system and the oxidase-based analyte electrode system.

In addition to measuring the fluid sample resistance between electrode area W1 and the reference electrode to compensate the sensor readings for blood hematocrit, oxidizable interferants such as ascorbic acid, uric acid and acetaminophen, to name a few, (which also cause inaccurate readings in the output of an electrochemical biosensor), can also be measured to compensate the sensor readings for these interferants. The interferant effect can be negated by subtracting the current response at W1 (first working electrode) from the current response from W2 (second working electrode) to calculate the concentration in the sample fluid. This is achieved by maintaining the surface area ratio of W1 and W2 constant. Although the glucose electrode measurements can be compensated for the above interferants by incorporating a similar reagent matrix (without the glucose oxidase) in W1 as the reagent matrix in the glucose electrode, it should be noted that oxygen sensor interferants can be compensated if W1 contains a similar reagent matrix (without the oxidase) in W1 as the reagent matrix in the oxygen electrode. Turning now to FIG. 17, there is illustrated a 4-layer configuration of another embodiment of the present invention showing a combination of an oxygen sensor system and an oxidase-based sensor system in a side-by-side configuration. FIG. 17 shows a combination oxygen/oxidase-based analyte sensor 700 with a laminated body 712, a fluid sampling end 714, an electrical contact end 716 and a vent opening 752. Sensor 700 may also include an optional inlet notch 754. Fluid sampling end 714 includes a first fluid sample channel 717a and a second fluid sample channel 717b between sample inlet 718 and vent opening 752. It should be understood that sample inlet 718 may optionally be two inlets (one for each of the fluid sample channels) adjacent each other and that vent opening 752 may also optionally incorporate separate vent openings for each of the fluid sample channels. In the illustrated embodiment, one of the fluid sample channels incorporates the oxygen sensor system and the other fluid sample channel incorporates the oxidase-based sensor system.

FIG. 18 shows an expanded view of laminated body 712 of the embodiment in FIG. 17. Laminated body 712 has a bottom layer 720, a reagent holding layer 730, a channel forming layer 740 with a fork-shaped cutout 742 having a first leg 742a and a second leg 742b that form fluid sample channels 717a, 717b, respectively, and a cover 750 with an optional inlet notch 754. Bottom layer 720 has a conductive layer 721 on which is delineated to at least four conductive paths 722, 724, 728, and 729. Conductive layer 721 may also include additional conductive paths 726, 727 to provide interferant and/or hematocrit compensating electrodes.

Reagent holding layer 730 has at least four reagent holding openings 732, 734, 738, and 739. Reagent holding opening 732 exposes a portion of conductive path 722, reagent holding opening 734 exposes a portion of conductive path 724, reagent holding opening 738 exposes a portion of conductive path 728, and reagent holding opening 739 exposes a portion of conductive path 729; all forming respective electrode reagent wells.

To include interferant and/or hematocrit compensation, reagent holding layer 730 would include additional reagent holding openings that would expose portions of other conductive paths such as, for example, conductive paths 726 and 727.

FIG. 19 illustrates a 3-layer configuration of another embodiment of the present invention showing a combination of an oxygen sensor system and an oxidase-based sensor system in a side-by-side configuration. FIG. 19 shows a combination oxygen/oxidase-based analyte sensor 800 with a laminated body 812, a fluid sampling end 814, an electrical contact end 816 and a vent opening 852. Sensor 800 may also include an optional inlet notch 854. Fluid sampling end 814 includes a first fluid sample channel 817a and a second fluid sample channel 817b between sample inlet 818 and vent opening 852. Like the 4-layer embodiment previously described, it should be understood that sample inlet 818 may optionally be two inlets (one for each of the fluid sample channels) adjacent each other and that vent opening 852 may also optionally incorporate separate vent openings for each of the fluid sample channels. In the illustrated embodiment, one of the fluid sample channels incorporates the oxygen sensor system and the other fluid sample channel incorporates the oxidase-based sensor system.

FIG. 20 shows an expanded view of laminated body 812 of the embodiment in FIG. 19. Laminated body 812 has a bottom layer 820, a channel forming layer 840 with a fork-shaped cutout 842 having a first leg 842a and a second leg 842b that form fluid sample channels 817a, 817b, respectively, and a cover 850 with an optional inlet notch 854. Bottom layer 820 has a conductive layer 821 on which is delineated to at least four conductive paths 822, 824, 828, and 829. Conductive layer 821 may also include additional conductive paths 826, 827 to provide additional electrode systems.

Assembly of the various embodiments of the present invention is relatively straightforward. For the 4-layer configuration, the bottom layer and reagent holding layer are laminated to each other followed by dispensing the reagent mixture into the reagent holding openings. After drying the reagent mixture, the channel forming layer is laminated onto the reagent holding layer and the cover is then laminated onto the channel forming layer. For the 3-layer construction, the bottom layer and the channel forming layer are laminated to each other followed by dispensing the reagent mixture into the U-shaped channel (or within each of the legs of the fork-shaped cutout of the side-by-side embodiment). After drying the reagent mixture, the cover is then laminated onto the channel forming layer.

The reagent mixture for the oxygen sensor includes at least an oxidase, a reduced form of a redox mediator and a peroxidase. The reagent mixture may optionally include one or more of a polymer, a surfactant, an inactive bulking agent, and an antioxidant.

The redox mediator may be any inorganic or organic redox species. Examples of usable redox mediators are potassium ferrocyanide, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, various ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone (BQ) where phen is 1,10-phenanthroline and bpy is 2,2'-bipyridine.

It is preferred that the mediator is capable of being oxidized chemically by hydrogen peroxide in the presence of peroxidase resulting from enzymatic reactions such as those illustrated in Eqs. (1) and (2) above. It is further desirable that the oxidized form of the mediator is capable of being reduced electrochemically at the working electrodes at the applied potential. It is still further desirable that the mediator is stable in the matrix. The preferred mediator in the present invention is potassium ferrocyanide ($K_4Fe(CN)_6$). The concentration of potassium ferrocyanide in the reagent mixture is preferably in a range of about 0.1% (W/W) to about 10%. More preferably, the concentration of potassium ferrocyanide is about 1%.

The polymers used as binders should be sufficiently water-soluble and should also be capable of stabilizing and binding all other chemicals in the reagent mixture in electrode areas W and R to the conductive surface coating. Although one or more polymer binders can be used in the reagent matrix, the preferred embodiment of the present invention uses two polymers as the reagent matrix binder. One of the preferred polymer binders is polyethylene oxide (PEO). Its molecular weight ranges from thousands to millions. Preferably, the molecular weight is over 1 million. More preferably, the molecular weight is about 4 million. The preferred PEO is a product available from Scientific Polymer Products, NY, USA (MW 4,000,000, Cat No. 344). The concentration of PEO in the reagent mixture is preferably in a range of about 0.04% (W/W) to about 2%. More preferably, the concentration of PEO is about 0.4%.

The second polymer binder is preferably methylcellulose, which is available under the brand name of Methocel 60 HG (Cat. No. 64655, Fluka Chemicals, Milwaukee, Wis., USA). The concentration of Methocel 60 HG in the reagent mixture is preferably in a range of about 0.05% (W/W) to about 5%. More preferably, the concentration of Methocel 60 HG is about 0.75%.

To stabilize the reduced form of the redox mediator, a small amount of an antioxidant is preferably added to the reagent mixture. The addition of a small amount of antioxidant to the reagent mixture provides for a long-term shelf life. The antioxidant must not interfere with the enzymatic reactions and the ensuing amperometric measurement. Antioxidants can be selected from, but are not limited to, various reductants and oxygen scavengers, such as sodium sulfite, sodium hydrosulfite, hydrazine, hydroquinone, carbohydrazide, N,N-Diethylhydroxylamine, methylethylketoxime, diethylthreitol, erythorbic acid, ascorbic acid. The preferred antioxidant in the present invention is sodium sulfite and is available from most chemical supply companies. The concentration of sodium sulfite in the reagent mixture is preferably in a range of about 0.01% (W/W) to about 1%. More preferably, the concentration of sodium sulfite is about 0.1%.

The optional surfactant facilitates dispensing of the reagent mixture into the reagent openings for the working and reference electrodes as well as for quickly dissolving the dry chemical reagents. The amount and type of surfactant is selected to assure the previously mentioned function and to avoid a denaturing effect on the enzymes. Surfactants can be selected from, but are not limited to, various anionic, cationic, non-ionic and zwitterionic detergents. Examples of surfactants include chemicals such as Triton X-100, Tween 20, sodium cholate hydrate, hexadecylpyridinium cholide monohydrate, CHAPs. The preferred surfactant is a polyoxyethylene ether. More preferably, it is t-octylphenoxypolyethoxyethanol and is available under the brand name Triton X-100. The concentration of Triton X-100 in the reagent mixture is preferably in a range of about 0.01% (W/W) to about 2%. More preferably, the concentration of Triton X-100 is about 0.4%.

A water soluble and inactive ingredient or bulking agent is preferably added into the reagent mixture to help prevent bubble entrapment at the electrode openings when a fluid sample fills the capillary channel. The bulking agent also should not react with other ingredients in the reagent mixture and should be inactive at the electrode surface. Examples of acceptable bulking agents include various sugars such as, for example, trehalose, galactose, sucrose, lactose, mannitol, mannose, fructose, sucrose, lactose, lactitol, sorbitol, and xylitol maltose, and the like. The preferred sugar is D(+) trehalose. The concentration of D(+) trehalose in the reagent mixture is preferably in a range of about 0.5% (W/W) to about 25%. More preferably, the concentration of D(+) trehalose is about 5%.

At least one oxidase must be included in the reagent matrix in order to produce hydrogen peroxide. The oxidase is selected from those capable of producing hydrogen peroxide such as, for example, glucose oxidase (GOD), acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, and xanthine oxidase. In the present invention, glucose oxidase (about 260 units per mg, Cat. No. GO3AC, Genzyme, USA) is used for illustration purposes. Any other oxidase may be used as long as the corresponding substrate concentration can be easily measured. The concentration of glucose oxidase in the preferred reagent mixture is preferably in a range of about 0.05% (W/W) to about 1.5%. More preferably, the concentration of glucose oxidase is about 0.24%.

Peroxidase is used to catalyze the reaction of hydrogen peroxide resulting from the enzymatic reaction with the reduced form of the redox mediator, ferrocyanide. Peroxidase may be from any source such as soybean (soybean peroxidase (SBP)) or horseradish root (horseradish root peroxidase (HRP)). The preferred peroxidase used in the present invention is HRP (about 126 units per mg, Cat. No. PEO 301) and is available from TOYOBO (Japan). The concentration of HRP in the reagent mixture is preferably in a range of about 0.1% (W/W) to about 3%. More preferably, the concentration of HRP is about 0.48%.

Accordingly, the preferred reagent mixture of the present invention contains about 0.75% (W/W) Methocel 60 HG, about 0.4% (W/W) polyethylene oxide, about 5% (W/W) D-(+) trehalose, about 0.4% (W/W) Triton X-100, about 0.1% (W/W) sodium sulfite, about 1% (W/W) potassium ferrocyanide, about 0.24% (W/W) glucose oxidase (about 624 units per mL reagent mixture), and about 0.48% (W/W) horseradish root peroxidase (about 605 units per mL reagent mixture).

Preparation of the Reagent Mixture

The reagent mixture is prepared in two steps:
Step 1: Into 100 ml of water, add 0.75 g Methocel 60 HG, 0.4 g polyethylene oxide, 5 g D-(+) trehalose, and 0.4 g Triton X-100. Stir the solution for 20 hrs.
Step 2: Into the above solution, add 0.1 g sodium sulfite, 1 g potassium ferrocyanide, 0.24 g glucose oxidase, and 0.48 g horseradish root peroxidase. Stir the solution for 10 min. The resulting solution is ready for dispensing.

Making of the Oxygen Sensor

For the 4-layer construction, about 60-100 nL of the reagent mixture is dispensed into the one of the reagent holding openings, the same amount of the reagent mixture is dispensed into the other reagent holding opening. For the 3-layer construction, about 1-3 µL of the reagent mixture is dispensed into the U-shaped channel that covers both working and reference electrode areas.

After the addition of the reagents to the electrode areas, the device is dried on a hot plate at a temperature of about 35-45° C. for about 1 minute. The drying time varies with the amount dispersed. For the 4-layer construction, after drying, the channel forming layer along with the cover is laminated onto the reagent holding layer. For the 3-layer construction, the cover is laminated onto the channel forming layer.

Although the description of electrode construction above describes construction for a single sensor, the design and materials used are ideal for making multiple sensors from one piece of each layer material. This would be accomplished by starting with a relatively large piece of base layer having a conducting layer thereon. A plurality of scored lines are made into the conductive layer such that a repetitive pattern is created using the preferred scribing method previously described whereby each pattern will eventually define the conductive paths for each sensor. Similarly, a large piece of the reagent holding layer material also having a plurality of openings in a repetitive pattern is sized to fit over the base layer in such a way that a plurality of sensors will be had when completed. The size of each aperture and the electrode material disposed in the plurality of electrode areas W and R are similar to that disclosed above. After disposing the reagent mixture in their respective reagent holding openings and dried, a large piece of the channel forming layer material having a plurality of elongated apertures is layered onto the reagent holding layer material such that each elongated aperture of the channel forming layer material contains corresponding openings of the reagent holding layer material. A comparably-sized cover layer material having a plurality of vent openings and notches in a repetitive pattern is layered onto the channel forming layer material. The laminated sheet is then cut in appropriate locations to form individual oxygen sensors.

Testing of the Oxygen Sensor

When a fluid sample is applied to a single strip of the present invention, the fluid sample enters the channel through the sample inlet and flows over the working and reference electrodes and stops at the threshold of the vent opening.

Chronoamperometry (i-t curve) was used to measure the current response of the oxygen sensors using an Electrochemical Analyzer (Model 812, CH Instruments, Austin, Tex., USA). Oxygen concentration ($pO_2$) was controlled using a Tonometer (Precision Gas Mixer, PGM-3, Medicor, Inc., Salt Lake City, Utah, USA). Once a blood sample enters the sensor, a potential of −0.3 Volts was applied across the working and the reference electrodes. The resultant current signals arising from the reduction of the oxidized form of the redox mediator are attributed to both oxygen concentration ($pO_2$) and glucose concentration in the blood sample. If not stated otherwise, the current at 20 seconds was recorded. The glucose concentration of the same blood sample was measured with a YSI glucose analyzer (Model 2300 Stat Plus, YSI Inc., Yellow Spring, Ohio).

Testing of the Glucose Strips

In order to correct the oxygen effect for an oxidase-based glucose sensor, glucose strips (based on the use of glucose oxidase) and meters produced by Nova Biomedical Corporation, Waltham, Mass., USA were used to demonstrate the unique feature of the oxygen effect correction. The blood samples vary both in glucose concentration and in oxygen concentration.

The following examples illustrate the unique features of the present invention.

EXAMPLE 1

Demonstration of Determination of Oxygen Concentration

Figure 21:
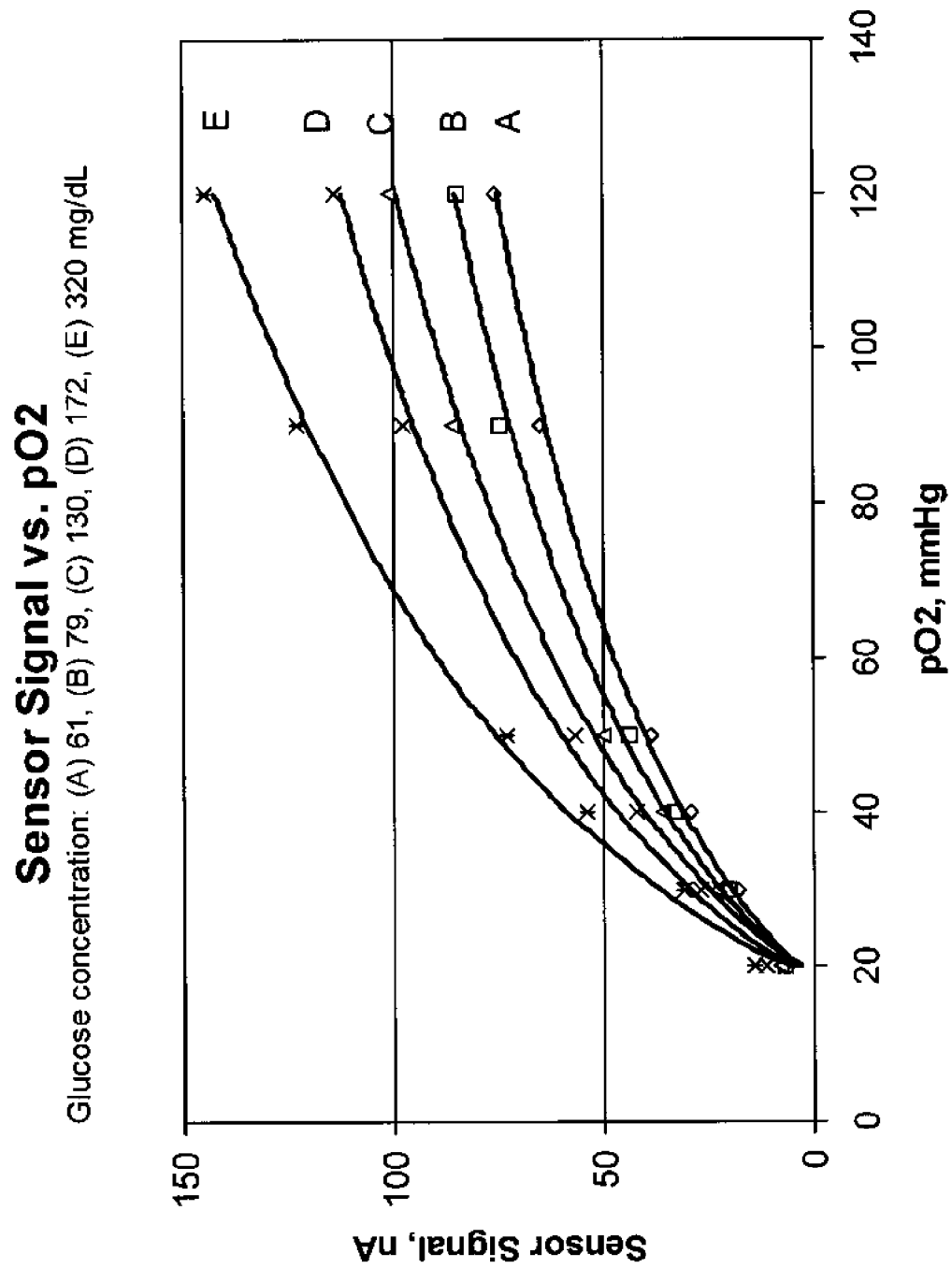
FIG. 21 shows the correlation between the sensor signal and the oxygen concentration.

Blood samples with different oxygen concentrations and different glucose concentrations were tested with the oxygen sensors of the present invention in connection with the Electrochemical Analyzer (CH Instruments, Model 812, Austin, Tex., USA). FIG. 21 shows the measured current response in nanoamperes of the oxygen sensors of the present invention to varying oxygen concentrations in the blood samples at five glucose concentrations, respectively.

As seen from the graph, the sensors of the present invention respond to the oxygen concentration in the blood samples over a range of about 20 to about 120 mmHg. Note that the responses are also dependent on the glucose concentration. Generally, the oxygen concentration can be expressed as a function of the current response and the glucose concentration as:

$$pO_2 = f(i,c) \qquad (3)$$

Where i is the current in nanoamps
c is the glucose concentration

The relationship among the oxygen concentration ($pO_2$, mmHg), glucose concentration and the current response for the particular oxygen sensor configuration used in the examples was determined from the empirical data to be $$pO_2 = ai^2 + bi + k_1 \qquad (4)$$

Where i is the current in nA; a and b are constants at a given glucose concentration defined by the following equations and $k_1$ equals 19.5.

$$a = 2 \times 10^{-7} C^2 - 9 \times 10^{-05} C + k_2 \qquad (5)$$

$$b = 2 \times 10^{-6} C^2 - k_3 C + k_4 \qquad (6)$$

Where C is the glucose concentration; $k_2$ equals 0.0172; $k_3$ equals 0.0015; $k_4$ equals 0.3739 for the particular configuration and sizing of the electrodes tested.

It should be understood that the constants are empirical constants based on data obtained from electrodes having certain size and dimension configurations and that changing the configuration of the spacing, surface area and size of the electrodes will change the constant values. These new values again would be determined by the empirical data for those electrodes.

Therefore, based on the testing results (current response and glucose concentration), the oxygen concentration ($pO_2$) can be easily calculated from Equations (4), (5) and (6).

Figure 22:
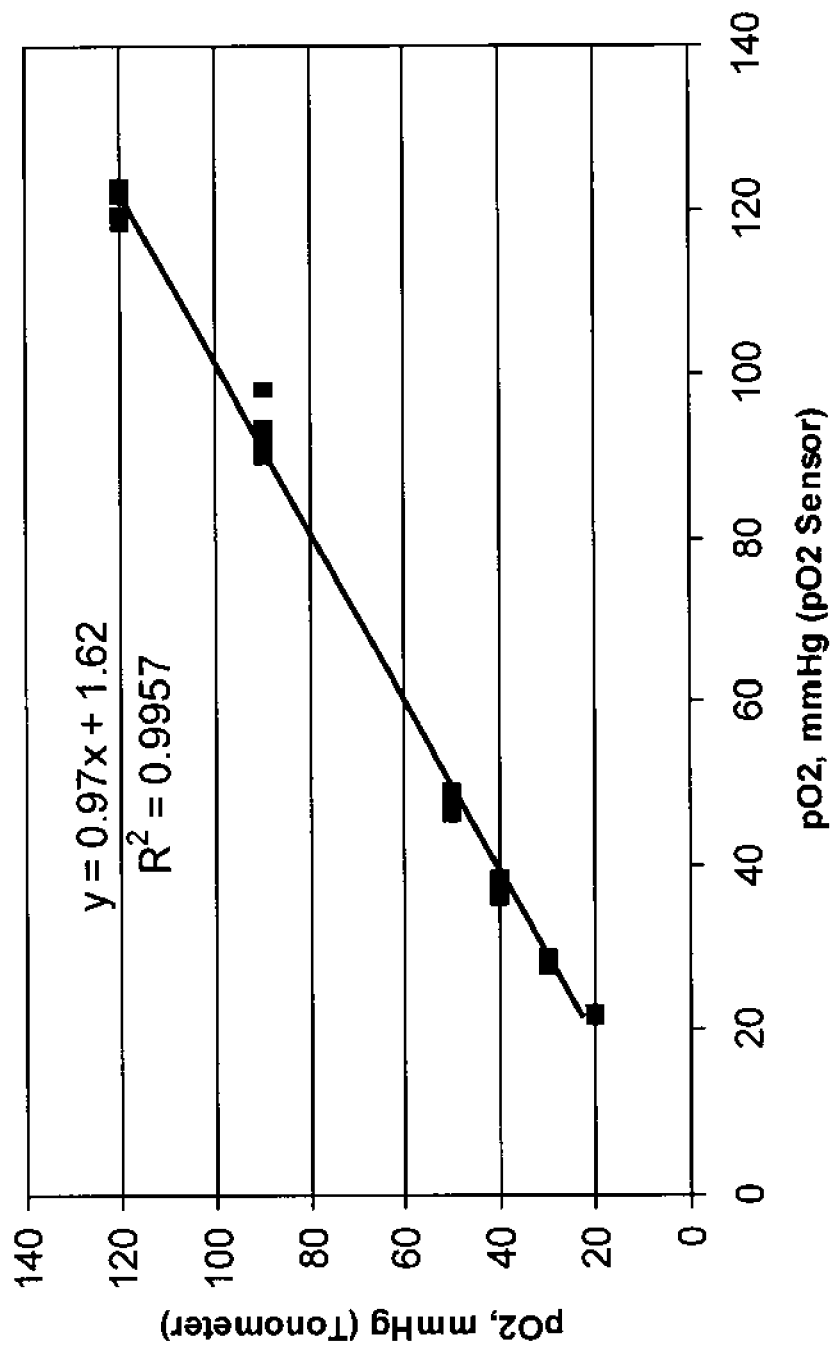
FIG. 22 shows the correlation between the oxygen sensor and tonometered oxygen.

FIG. 22 shows the correlation between oxygen sensors and tonometered oxygen over an oxygen range of about 20 to about 120 mm Hg. The regression equation is $$pO_2(\text{Tonometer}) = 0.97 pO_2 (\text{sensor}) + 1.62 \tag{7}$$

with a square regression constant ($R^2$) of 0.9957. The results indicate that the oxygen sensors respond to the oxygen concentration accurately.

EXAMPLE 2

Figure 23:
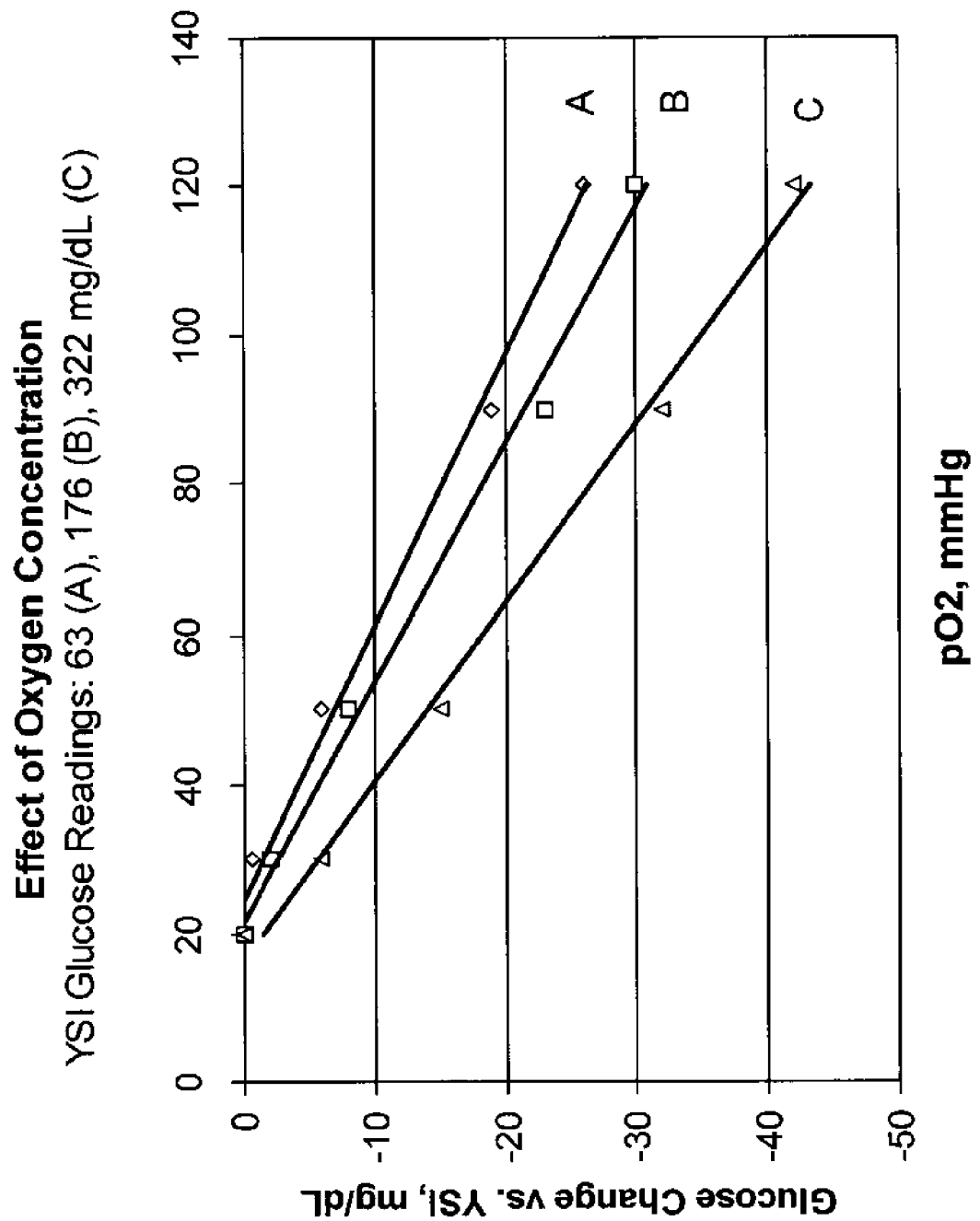
FIG. 23 shows the effect of oxygen concentration on glucose measurements.

Demonstration of the Correlation Between Oxygen Concentration and Oxygen Effect of Glucose Sensors The glucose meter/strip produced by Nova Biomedical Corporation was used to study the oxygen effect. The oxygen concentration in the blood samples was varied from about 20 to about 120 mmHg at the glucose concentration of 63, 176, 322 mg/dL, respectively. The glucose concentrations of the same blood samples were also measured with the YSI glucose analyzer. FIG. 23 shows the change in the glucose readings with the glucose meter/strip against the YSI meter readings. As expected, the meter readings decrease with increasing the oxygen concentration. Note that such a change is also glucose-concentration dependent.

The change in glucose can be represented by a generic equation such as:

$$\Delta\text{Glucose (mg/dL)} = (aC^2 + bC + k_5) pO_2 + D \tag{8}$$

Where $a$, $b$, $k_5$ and $D$ are constants at given conditions.

At a given glucose concentration, the glucose correction factor (vs. YSI reading) displays a linear relationship with $pO_2$, as shown in the following equation:

$$\Delta\text{Glucose correction factor (mg/dL)} = (-2 \times 10^{-06} C^2 + 3 \times 10^{-05} C - k_6) pO_2 + k_7 \tag{9}$$

Where C is the glucose concentration (mg/dL) before the oxygen effect correction, which can be obtained from the glucose meter/strip;

$pO_2$ (mmHg) is the partial pressure of oxygen, which can be obtained from the $pO_2$ sensor of the present invention; $k_6$ equals 0.272; $k_7$ equals 6.87 for the particular electrode configuration tested.

EXAMPLE 3

Demonstration of the Correction of the Oxygen Effect

Figure 24:
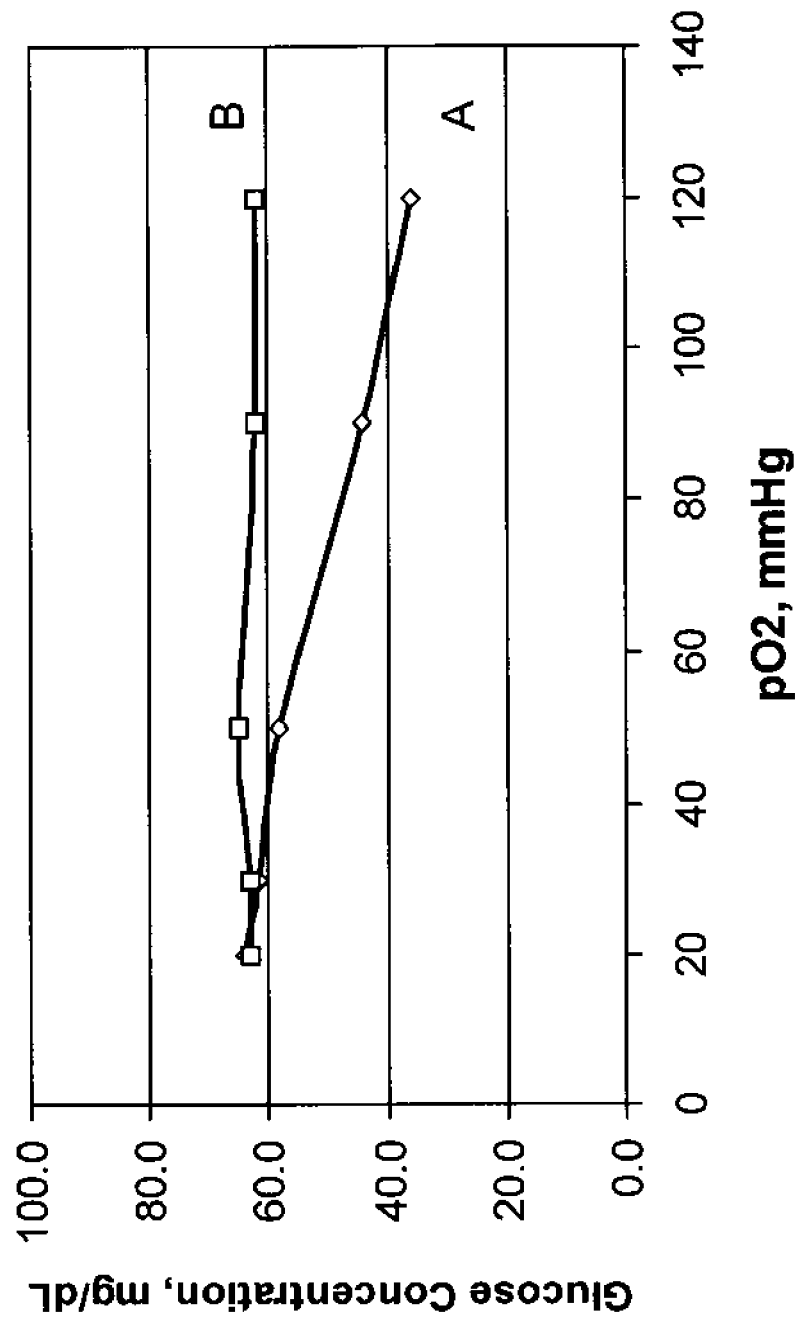
FIG. 24 shows the correction of the oxygen effect at glucose concentration of about 60 mg/dL.
Figure 25:
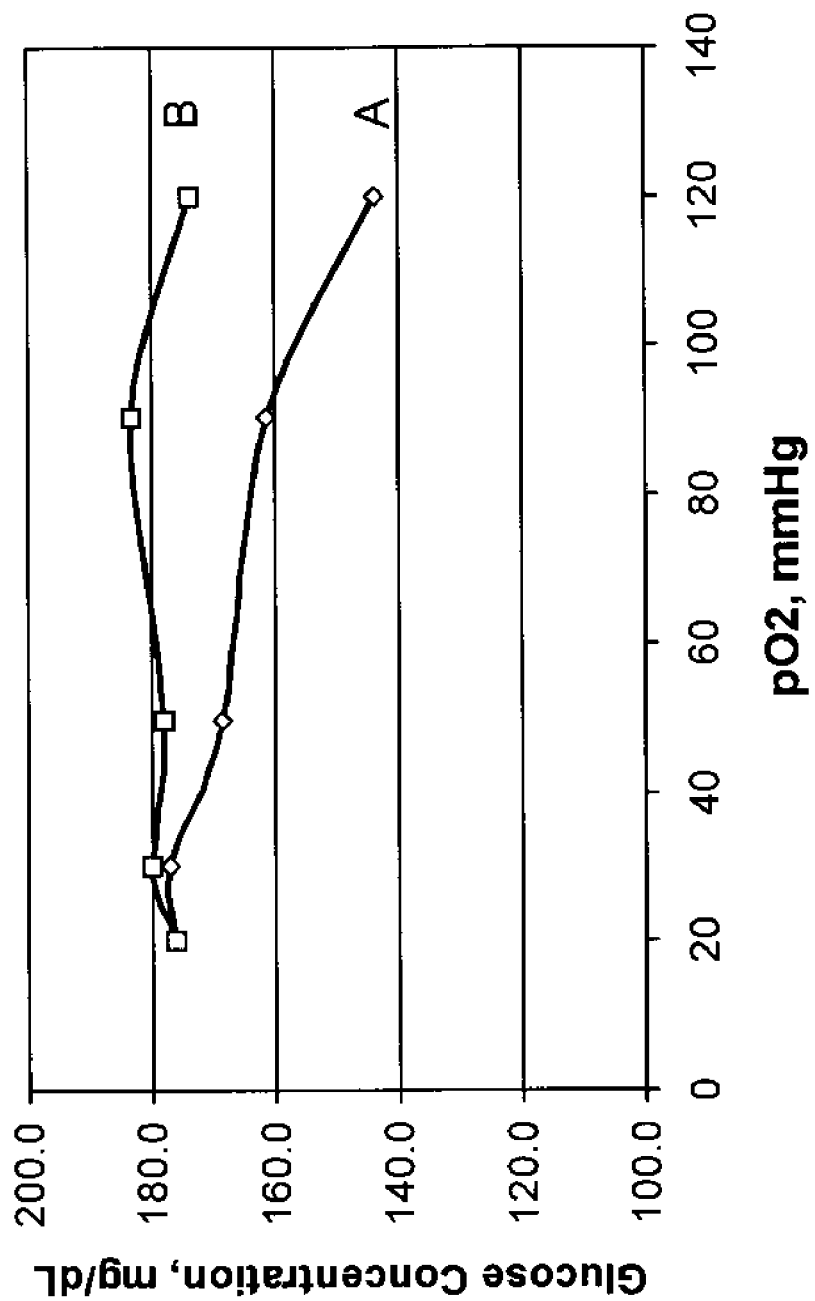
FIG. 25 shows the correction of the oxygen effect at glucose concentration of about 180 mg/dL.
Figure 26:
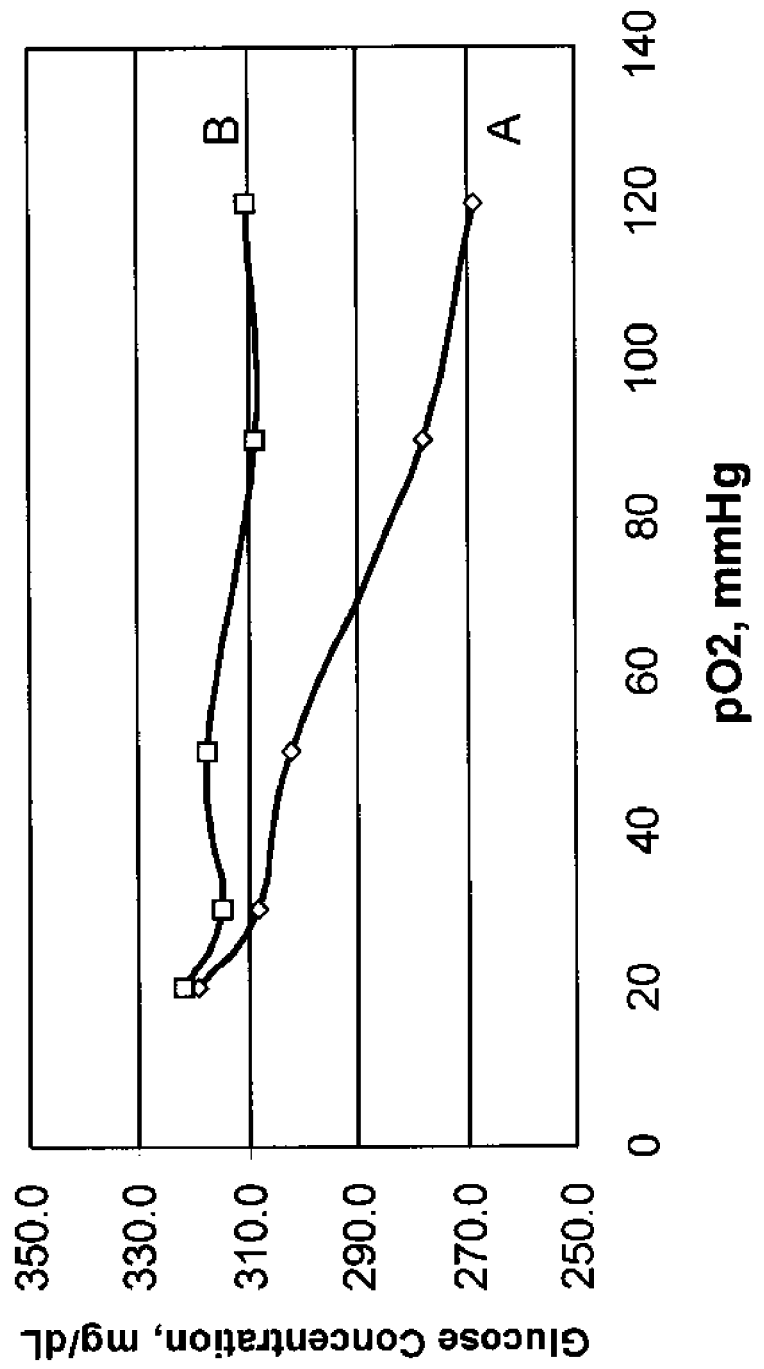
FIG. 26 shows the correction of the oxygen effect at glucose concentration of about 320 mg/dL.

Once the oxygen concentration, $pO_2$, and the correlation between oxygen concentration and oxygen effect of the particular glucose sensors used are known, the oxygen effect can be corrected using the glucose correction factor (Eq. (9)) to the meter readings. The blood samples of three glucose concentrations were tested by varying the oxygen concentration from about 20 to about 120 mmHg. The results are shown in FIGS. 24-26. Curves A and B indicate the results before and after the oxygen effect correction, respectively. It is clear from the data that the correction of the oxygen effect in the present invention eliminates the interference caused by varying oxygen concentrations.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of correcting the oxygen effect on oxidase-based analyte sensors comprising:
   determining an oxygen concentration of a fluid sample using an oxygen sensor comprising a working electrode, a reference electrode and a reagent matrix disposed on at least said working electrode wherein said reagent matrix contains a reduced form of a redox mediator, an oxidase and a peroxidase and wherein said oxygen sensor has a known correlation between oxygen concentration and analyte concentration expressed as a function of the response of said oxygen sensor to both oxygen and an analyte wherein said analyte is a substrate of said oxidase;
   using an oxidased-based analyte sensor wherein the correlation between oxygen concentration and oxygen effect on said oxidase-based analyte sensor is known and wherein an oxidase in said oxidased-based sensor is a substrate of said oxidase in said oxygen sensor;
   determining an analyte concentration of said fluid sample using said oxidase-based analyte sensor; and
   calculating a corrected analyte concentration in said fluid sample using said determined oxygen concentration.

2. The method of claim 1 wherein said oxygen concentration determining step further includes applying a potential between said reference electrode and said working electrode, measuring a first current generated between said working electrode and said reference electrode, and correlating said first current to a concentration of oxygen in said fluid sample using said function.

3. The method of claim 2 wherein said oxygen concentration determining step further includes deriving said function as an oxygen empirical equation used for determining said oxygen concentration based on the configuration of said oxygen sensor.

4. The method of claim 3 wherein said oxygen empirical equation is represented by the formula $$pO_2 = ai^2 + bi + k_1$$

where $a$ and $b$ are empirical constants at a given glucose concentration determined by the configuration of said oxygen sensor, $k_1$ is an empirical constant based on electrode configuration, and $i$ is the current measured by said oxygen sensor.

5. The method of claim 1 wherein said calculating step further includes determining a correction factor for said analyte to be added to said determined analyte concentration.

6. The method of claim 5 wherein said correction factor further includes determining an analyte empirical equation used for determining said correction factor of said analyte concentration based on the configuration of said oxidase-based analyte sensor.

7. The method of claim 6 wherein said analyte empirical equation is represented by the formula $$\Delta C = (-2 \times 10^{-06} C^2 + 3 \times 10^{-05} C - k_6) pO_2 + k_7$$

where C is said determined analyte concentration before correction, $pO_2$ is said determined oxygen concentration, and $k_6$ and $k_7$ are empirical constants based on electrode configuration.

8. A system for correcting the oxygen effect on oxidase-based analyte sensors, said system comprising:
an oxygen sensor comprising a working electrode, a reference electrode and a reagent matrix disposed on at least said working electrode wherein said reagent matrix contains a reduced form of a redox mediator, an oxidase and a peroxidase wherein said oxygen sensor has a known correlation between oxygen concentration and analyte concentration expressed as a function of the response of said oxygen sensor to both oxygen and an analyte wherein said analyte is a substrate of said oxidase;
an oxidase-based analyte sensor for measuring an analyte in a portion of a fluid sample wherein said analyte is a substrate of said oxidase in said oxygen sensor and wherein the correlation between oxygen concentration and oxygen effect on said oxidase-based analyte sensor is known;
means for electronically determining an oxygen concentration in a portion of said fluid sample using said oxygen sensor;
means for electronically determining an analyte concentration in another portion of said fluid sample using said oxidase-based analyte sensor; and
means for using said determined oxygen concentration in said fluid sample to determine a corrected value of said analyte concentration in said fluid sample.

9. The system of claim 8 wherein said reagent matrix of said oxygen sensor further includes one or more of a material selected from the group consisting of a surfactant, a polymer binder, an inactive bulking agent, and an antioxidant.

10. The system of claim 8 wherein said reduced form of said redox mediator is capable of being oxidized by hydrogen peroxide.

11. The system of claim 10 wherein said reduced form of said redox mediator is selected from the group consisting of potassium ferrocyanide, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone wherein phen is 1,10-phenanthroline and bpy is 2,2'-bipyridine.

12. The system of claim 8 wherein said oxidase of said oxygen sensor is capable of producing hydrogen peroxide.

13. The system of claim 12 wherein said oxidase of said oxygen sensor is selected from the group consisting of glucose oxidase, acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, and xanthine oxidase.

14. The system of claim 8 wherein said peroxidase of said oxygen sensor is selected from the group consisting of soybean peroxidase and horseradish root peroxidase.

15. The system of claim 8 wherein said means for determining said oxygen concentration includes an oxygen empirical equation based on empirical data obtained with the configuration of said oxygen sensor.

16. The system of claim 15 wherein said oxygen empirical equation is represented by the formula $$pO_2 = ai^2 + bi + k_1$$

where a and b are empirical constants at a given glucose concentration in milligrams per deciliter determined by the configuration of said oxygen sensor, $k_1$ is an empirical constant based on electrode configuration, and i is the current in nanoamps measured by said oxygen sensor.

17. The system of claim 8 wherein said means for using said oxygen concentration to determine a corrected analyte concentration further includes an analyte empirical equation to determine a correction factor based on empirical data obtained with the configuration of said oxidased-based analyte sensor.

18. The system of claim 17 wherein said analyte empirical equation is represented by the formula $$\Delta C = (-2 \times 10^{-06} C^2 + 3 \times 10^{-05} C - k_6) pO_2 + k_7$$

where C is said determined analyte concentration before correction, $pO_2$ is said determined oxygen concentration, and $k_6$ and $k_7$ are empirical constants based on electrode configuration.

19. The system of claim 9 wherein said polymer binder is selected from the group consisting of polyvinylpyrrolidone, polyethylene oxide, poly(vinyl alcohol), poly(ethylene glycol), poly(propylene glycol), polysulfone, carboxy methyl cellulose, hydroxypropyl cellulose, methyl cellulose, poly(2-ethyl-2oxazoline).

20. The system of claim 9 wherein said polymer binder is a mixture of polyethylene oxide and methyl cellulose.

21. The system of claim 9 wherein said surfactant is selected from the group consisting of anionic, cationic, nonionic, and zwitterionic detergents.

22. The system of claim 9 wherein said surfactant is selected from the group consisting of Triton X-100, Tween 20, sodium cholate hydrate, hexadecylpyridinium cholide monohydrate, and CHAPs.

23. The system of claim 9 wherein said inactive bulking agent is a sugar.

24. The system of claim 23 wherein said sugar is selected from the group consisting of trehalose, galactose, suctose, lactose, mannitol, mannose, fructose, sucrose, lactose, lactitol, sorbitol, xylitol, and maltose.

25. The system of claim 9 wherein said antioxidant is selected from the group consisting of reductants and oxygen scavengers.

26. The system of claim 9 wherein said antioxidant is selected from the group consisting of sodium sulfite, sodium hydrosulfite, hydrazine, hydroquinone, carbohydrazide, N,N-Diethylhydroxylamine, methylethylketoxime, diethylthreitol, erythorbic acid, and ascorbic acid.

27. A combination for correcting the oxygen effect on oxidase-based analyte sensors, the combination comprising:
a disposable sensor strip comprising:
an oxygen electrode with an oxygen reagent matrix disposed thereon, said oxygen reagent matrix includes a reduced form of a redox mediator, an oxidase and a peroxidase wherein said oxygen sensor has a known correlation between oxygen concentration and analyte concentration expressed as a function of the response of said oxygen sensor to both oxygen and an analyte wherein said analyte is a substrate of said oxidase;
an oxidase-based analyte electrode with an oxidase-based reagent matrix thereon, said oxidase-based reagent matrix includes an oxidized form of a redox mediator and an enzyme capable of catalyzing a reaction involving a substrate for said oxidase of said oxygen electrode and wherein the correlation between oxygen concentration and oxygen effect on said oxidase-based analyte sensor is known;

a reference electrode; and a sample chamber containing said oxygen electrode, said oxidase-based analyte electrode and said reference electrode; and meter means for electronically coupling said oxygen electrode and said reference electrode to measure an oxygen concentration in a sample fluid, for electronically coupling said oxidased-based analyte electrode to said reference electrode to measure an analyte concentration in said sample fluid, and for electronically calculating a corrected analyte concentration in said fluid sample using said measured oxygen concentration.

28. The combination of claim 27 wherein said oxygen reagent matrix of said oxygen sensor further includes one or more of a material selected from the group consisting of a surfactant, a polymer binder, an inactive bulking agent, and an antioxidant.

29. The combination of claim 27 wherein said reduced form of said redox mediator is capable of being oxidized by hydrogen peroxide.

30. The combination of claim 29 wherein said reduced form of said redox mediator is selected from the group consisting of potassium ferrocyanide, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2CL]^+$, $[Ru(bpy)_2]^{2+}$, $[Rh(bpy)_2]^{2+}$, cobalt phthalocyanine, ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone wherein phen is 1,10-phenanthroline and bpy is 2,2'-bipyridine.

31. The combination of claim 27 wherein said oxidase of said oxygen sensor is capable of producing hydrogen peroxide.

32. The combination of claim 31 wherein said oxidase of said oxygen sensor is selected from the group consisting of glucose oxidase, acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, and xanthine oxidase.

33. The combination of claim 27 wherein said peroxidase of said oxygen sensor is selected from the group consisting of soybean peroxidase and horseradish root peroxidase.

* * * * *

UNITED STATES PATENT AND TRADEMARK OFFICE
CERTIFICATE OF CORRECTION

PATENT NO. : 7,611,621 B2
APPLICATION NO. : 11/160193
DATED : November 3, 2009
INVENTOR(S) : Cai et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1153 days.

Signed and Sealed this

Twelfth Day of October, 2010

David J. Kappos
*Director of the United States Patent and Trademark Office*